United States Patent
Ciaramella et al.

(10) Patent No.: US 11,207,398 B2
(45) Date of Patent: *Dec. 28, 2021

(54) ZIKA VIRUS MRNA VACCINES

(71) Applicant: ModernaTX, Inc., Cambridge, MA (US)

(72) Inventors: Giuseppe Ciaramella, Sudbury, MA (US); Sunny Himansu, Winchester, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,318

(22) Filed: Apr. 14, 2020

(65) Prior Publication Data

US 2020/0276296 A1 Sep. 3, 2020

Related U.S. Application Data

(62) Division of application No. 16/131,793, filed on Sep. 14, 2018, now Pat. No. 10,653,767.

(60) Provisional application No. 62/558,746, filed on Sep. 14, 2017.

(51) Int. Cl.
  *A61K 39/12* (2006.01)
  *A61P 31/14* (2006.01)
  *A61K 39/00* (2006.01)

(52) U.S. Cl.
  CPC .............. *A61K 39/12* (2013.01); *A61P 31/14* (2018.01); *A61K 2039/53* (2013.01); *A61K 2039/54* (2013.01); *A61K 2039/545* (2013.01); *A61K 2039/575* (2013.01); *C12N 2770/24134* (2013.01)

(58) Field of Classification Search
  None
  See application file for complete search history.

(56) References Cited

U.S. PATENT DOCUMENTS

| | | |
|---|---|---|
| 3,906,092 A | 9/1975 | Hilleman et al. |
| 6,500,419 B1 | 12/2002 | Hone et al. |
| 6,514,948 B1 | 2/2003 | Raz et al. |
| 6,610,044 B2 | 8/2003 | Mathiesen |
| 7,001,890 B1 | 2/2006 | Wagner et al. |
| 8,217,016 B2 | 7/2012 | Hoerr et al. |
| 8,569,256 B2 | 10/2013 | Heyes et al. |
| 8,609,142 B2 | 12/2013 | Troiano et al. |
| 8,613,954 B2 | 12/2013 | Zale et al. |
| 8,617,608 B2 | 12/2013 | Zale et al. |
| 8,673,316 B2 | 3/2014 | Kinney et al. |
| 8,691,961 B1 | 4/2014 | Puffer et al. |
| 8,710,200 B2 | 4/2014 | Schrum et al. |
| 8,734,832 B2 | 5/2014 | O'Hagan et al. |
| 8,734,853 B2 | 5/2014 | Sood et al. |
| 8,754,062 B2 | 6/2014 | de Fougerolles et al. |
| 8,822,663 B2 | 9/2014 | Schrum et al. |
| 8,999,380 B2 | 4/2015 | Bancel et al. |
| 9,000,141 B2 | 4/2015 | Chang et al. |
| 9,221,891 B2 | 12/2015 | Bancel et al. |
| 9,267,114 B2 | 2/2016 | Yamshchikov et al. |
| 9,283,287 B2 | 3/2016 | Bancel et al. |
| 9,303,079 B2 | 4/2016 | Bancel et al. |
| 9,464,124 B2 | 10/2016 | Bancel et al. |
| 9,512,456 B2 | 12/2016 | Wang et al. |
| 9,533,047 B2 | 1/2017 | de Fougerolles et al. |
| 9,597,380 B2 | 3/2017 | Chakraborty et al. |
| 9,868,691 B2 | 1/2018 | Benenato et al. |
| 9,872,900 B2 | 1/2018 | Ciaramella et al. |
| 10,064,934 B2 | 9/2018 | Ciaramella et al. |
| 10,064,935 B2 | 9/2018 | Ciaramella et al. |
| 10,124,055 B2 | 11/2018 | Ciaramella et al. |
| 10,207,010 B2 | 2/2019 | Besin et al. |
| 10,232,055 B2 | 3/2019 | Kariko et al. |
| 10,273,269 B2 | 4/2019 | Ciaramella |
| 10,286,086 B2 | 5/2019 | Roy et al. |
| 10,385,088 B2 | 8/2019 | Fraley et al. |
| 10,449,244 B2 | 10/2019 | Ciaramella et al. |
| 10,465,190 B1 | 11/2019 | Chen et al. |
| 10,493,143 B2 | 12/2019 | Ciaramella et al. |
| 10,526,629 B2 | 1/2020 | Rabideau et al. |
| 10,653,712 B2 | 5/2020 | Hoge |
| 10,653,767 B2 | 5/2020 | Ciaramella et al. |
| 10,695,419 B2 | 6/2020 | Ciaramella et al. |
| 10,857,105 B2 | 12/2020 | Benenato et al. |
| 10,925,958 B2 | 2/2021 | Ciaramella |
| 2001/0001066 A1 | 5/2001 | Cezayirli et al. |
| 2003/0032615 A1 | 2/2003 | Felgner et al. |
| 2003/0092653 A1 | 5/2003 | Kisich et al. |
| 2004/0005667 A1 | 1/2004 | Ratti et al. |
| 2005/0032730 A1 | 2/2005 | Von Der Mulbe et al. |
| 2005/0059624 A1 | 3/2005 | Hoerr et al. |

(Continued)

FOREIGN PATENT DOCUMENTS

| AU | 652831 B2 | 9/1994 |
|---|---|---|
| AU | 2015210364 A1 | 3/2017 |

(Continued)

OTHER PUBLICATIONS

International Search Report and Written Opinion for Application No. PCT/US2018/051120, dated Dec. 24, 2018.

[No Author Listed], "Messenger RNA", Internet: Wikipedia. Jun. 19, 2013, XP002699196, Retrieved from the Internet: URL: http://en.wikipedia.org/wiki/Messenger RNA.

(Continued)

*Primary Examiner* — Benjamin P Blumel

(74) *Attorney, Agent, or Firm* — Wolf, Greenfield & Sacks, P.C.

(57) ABSTRACT

Provided herein, in some embodiments, are Zika virus RNA vaccines and methods of producing an antigen-specific immune response in a subject.

25 Claims, 2 Drawing Sheets

Specification includes a Sequence Listing.

(56) References Cited

U.S. PATENT DOCUMENTS

| | | |
|---|---|---|
| 2005/0250723 A1 | 11/2005 | Hoerr et al. |
| 2006/0172003 A1 | 8/2006 | Meers et al. |
| 2006/0172966 A1 | 8/2006 | Lipford et al. |
| 2007/0280929 A1 | 12/2007 | Hoerr et al. |
| 2007/0292453 A1 | 12/2007 | Floyd et al. |
| 2008/0025944 A1 | 1/2008 | Hoerr et al. |
| 2008/0171711 A1 | 7/2008 | Hoerr et al. |
| 2010/0130588 A1 | 5/2010 | Yaworski et al. |
| 2010/0189729 A1 | 7/2010 | Hoerr et al. |
| 2010/0203076 A1 | 8/2010 | Fotin-Mleczek et al. |
| 2010/0239608 A1 | 9/2010 | Von Der Mulbe et al. |
| 2010/0291156 A1 | 11/2010 | Barner et al. |
| 2010/0303851 A1 | 12/2010 | Hoerr et al. |
| 2010/0305196 A1 | 12/2010 | Probst et al. |
| 2011/0250225 A1 | 10/2011 | Fotin-Mleczek et al. |
| 2011/0269950 A1 | 11/2011 | Von Der Mulbe et al. |
| 2011/0311472 A1 | 12/2011 | Hoerr et al. |
| 2012/0009221 A1 | 1/2012 | Hoerr et al. |
| 2012/0101148 A1 | 4/2012 | Aking et al. |
| 2012/0189700 A1 | 7/2012 | Aguilar et al. |
| 2012/0219573 A1 | 8/2012 | Baumhof et al. |
| 2012/0258046 A1 | 10/2012 | Mutske |
| 2013/0022538 A1 | 1/2013 | Rossi |
| 2013/0102034 A1 | 4/2013 | Schrum et al. |
| 2013/0121988 A1 | 5/2013 | Hoerr et al. |
| 2013/0142818 A1 | 6/2013 | Baumhof et al. |
| 2013/0156849 A1 | 6/2013 | de Fougerolles et al. |
| 2013/0171241 A1 | 7/2013 | Geall |
| 2013/0183355 A1 | 7/2013 | Jain et al. |
| 2013/0189351 A1 | 7/2013 | Geall |
| 2013/0195867 A1 | 8/2013 | Hoerr et al. |
| 2013/0195967 A1 | 8/2013 | Guild et al. |
| 2013/0195968 A1 | 8/2013 | Geall et al. |
| 2013/0195969 A1 | 8/2013 | Geall et al. |
| 2013/0202684 A1 | 8/2013 | Geall et al. |
| 2013/0236533 A1 | 9/2013 | Von Andrian et al. |
| 2013/0236974 A1 | 9/2013 | De Fougerolles |
| 2013/0243848 A1 | 9/2013 | Lobovkina et al. |
| 2013/0245103 A1 | 9/2013 | de Fougerolles et al. |
| 2013/0259923 A1 | 10/2013 | Bancel et al. |
| 2013/0266640 A1 | 10/2013 | De Fougerolles et al. |
| 2013/0295043 A1 | 11/2013 | Kallen et al. |
| 2013/0336998 A1 | 12/2013 | Kallen et al. |
| 2014/0037660 A1 | 2/2014 | Folin-Mleczek et al. |
| 2014/0065228 A1 | 3/2014 | Yarowoski et al. |
| 2014/0134201 A1 | 5/2014 | Tureci et al. |
| 2014/0147432 A1 | 5/2014 | Bancel et al. |
| 2014/0148502 A1 | 5/2014 | Bancel et al. |
| 2014/0193482 A1 | 7/2014 | Bancel et al. |
| 2014/0206752 A1 | 7/2014 | Afeyan et al. |
| 2014/0206753 A1 | 7/2014 | Guild et al. |
| 2014/0271829 A1 | 9/2014 | Lilja et al. |
| 2014/0308304 A1 | 10/2014 | Manoharan et al. |
| 2014/0378538 A1 | 12/2014 | Bancel |
| 2015/0051268 A1 | 2/2015 | Bancel et al. |
| 2015/0056253 A1 | 2/2015 | Bancel et al. |
| 2015/0141499 A1 | 5/2015 | Bancel et al. |
| 2015/0307542 A1 | 10/2015 | Roy et al. |
| 2015/0315541 A1 | 11/2015 | Bancel et al. |
| 2016/0024140 A1 | 1/2016 | Issa et al. |
| 2016/0024141 A1 | 1/2016 | Issa et al. |
| 2016/0032273 A1 | 2/2016 | Shahrokh et al. |
| 2016/0038612 A1 | 2/2016 | Hoge et al. |
| 2016/0243221 A1 | 8/2016 | Hoge et al. |
| 2016/0271272 A1 | 9/2016 | Bancel et al. |
| 2016/0317647 A1 | 11/2016 | Ciaramella et al. |
| 2016/0331828 A1 | 11/2016 | Ciaramella et al. |
| 2016/0367658 A1 | 12/2016 | Kinney et al. |
| 2017/0043037 A1 | 2/2017 | Kariko et al. |
| 2017/0065675 A1 | 3/2017 | Bancel et al. |
| 2017/0130255 A1 | 5/2017 | Wang et al. |
| 2017/0202979 A1 | 7/2017 | Chakraborty et al. |
| 2017/0340724 A1 | 11/2017 | Ciaramella et al. |
| 2017/0340725 A1 | 11/2017 | Ciaramella et al. |
| 2018/0000953 A1 | 1/2018 | Almarsson et al. |
| 2018/0002393 A1 | 1/2018 | Bancel et al. |
| 2018/0028645 A1 | 2/2018 | Ciaramella et al. |
| 2018/0028664 A1 | 2/2018 | Besin et al. |
| 2018/0237849 A1 | 8/2018 | Thompson |
| 2018/0243225 A1 | 8/2018 | Ciaramella |
| 2018/0243230 A1 | 8/2018 | Smith |
| 2018/0256628 A1 | 9/2018 | Hoge et al. |
| 2018/0271795 A1 | 9/2018 | Martini et al. |
| 2018/0271970 A1 | 9/2018 | Ciaramella et al. |
| 2018/0273977 A1 | 9/2018 | Mousavi et al. |
| 2018/0274009 A1 | 9/2018 | Marquardt et al. |
| 2018/0280496 A1 | 10/2018 | Ciaramella et al. |
| 2018/0289792 A1 | 10/2018 | Ciaramella et al. |
| 2018/0303929 A1 | 10/2018 | Ciaramella et al. |
| 2018/0311336 A1 | 11/2018 | Ciaramella et al. |
| 2018/0311343 A1 | 11/2018 | Huang et al. |
| 2018/0312549 A1 | 11/2018 | Ciaramella |
| 2018/0318409 A1 | 11/2018 | Valiante et al. |
| 2018/0363019 A1 | 12/2018 | Hoge |
| 2018/0369374 A1 | 12/2018 | Frederick et al. |
| 2018/0371047 A1 | 12/2018 | Ticho et al. |
| 2019/0002890 A1 | 1/2019 | Martini et al. |
| 2019/0008938 A1 | 1/2019 | Ciaramella et al. |
| 2019/0085368 A1 | 3/2019 | Bancel et al. |
| 2019/0099481 A1 | 4/2019 | Ciaramella et al. |
| 2019/0175517 A1 | 6/2019 | Martini et al. |
| 2019/0175727 A1 | 6/2019 | Huang et al. |
| 2019/0192646 A1 | 6/2019 | Cohen et al. |
| 2019/0192653 A1 | 6/2019 | Hoge et al. |
| 2019/0275170 A1 | 9/2019 | Benenato et al. |
| 2019/0298657 A1 | 10/2019 | Martini et al. |
| 2019/0298658 A1 | 10/2019 | Benenato |
| 2019/0300906 A1 | 10/2019 | Martini et al. |
| 2019/0314292 A1 | 10/2019 | Benenato et al. |
| 2019/0336595 A1 | 11/2019 | Ciaramella |
| 2019/0351040 A1 | 11/2019 | Valiante et al. |
| 2019/0382774 A1 | 12/2019 | Hoge et al. |
| 2019/0390181 A1 | 12/2019 | Benenato et al. |
| 2020/0030432 A1 | 1/2020 | Ciaramella et al. |
| 2020/0032274 A1 | 1/2020 | Mauger et al. |
| 2020/0038499 A1 | 2/2020 | Narayanan et al. |
| 2020/0054737 A1 | 2/2020 | Ciaramella et al. |
| 2020/0069599 A1 | 3/2020 | Smith et al. |
| 2020/0069793 A1 | 3/2020 | Ciaramella |
| 2020/0069794 A1 | 3/2020 | Ciaramella et al. |
| 2020/0071689 A1 | 3/2020 | Miracco |
| 2020/0085916 A1 | 3/2020 | Martini et al. |
| 2020/0109420 A1 | 4/2020 | Brito et al. |
| 2020/0129608 A1 | 4/2020 | Ciaramella et al. |
| 2020/0129615 A1 | 4/2020 | Ciaramella et al. |
| 2020/0163878 A1 | 5/2020 | Baumhof et al. |
| 2020/0239869 A1 | 7/2020 | Issa et al. |
| 2020/0254086 A1 | 8/2020 | Hoge et al. |
| 2020/0282047 A1 | 9/2020 | Ciaramella et al. |
| 2020/0368343 A1 | 11/2020 | Ciaramella et al. |
| 2021/0046173 A1 | 2/2021 | Ciaramella et al. |
| 2021/0163919 A1 | 6/2021 | Issa et al. |

FOREIGN PATENT DOCUMENTS

| | | |
|---|---|---|
| CA | 2473135 | 6/2003 |
| EP | 1026253 | 8/2000 |
| EP | 1083232 | 2/2005 |
| EP | 1301614 B1 | 11/2006 |
| EP | 1383556 B1 | 10/2007 |
| EP | 1905844 A2 | 2/2008 |
| EP | 2188379 B1 | 1/2013 |
| EP | 2548960 A1 | 1/2013 |
| WO | WO 1987/005326 | 9/1987 |
| WO | WO 1990/11092 | 10/1990 |
| WO | WO 1990/011092 A1 | 10/1990 |
| WO | WO 1993/14778 | 8/1993 |
| WO | WO 1993/014778 A1 | 8/1993 |
| WO | WO 1995/24485 | 9/1995 |
| WO | WO 1995/024485 A2 | 9/1995 |
| WO | WO 1995/26204 | 10/1995 |
| WO | WO 1995/026204 A1 | 10/1995 |
| WO | WO 1995/33835 | 12/1995 |
| WO | WO 1995/033835 A1 | 12/1995 |

(56) References Cited

FOREIGN PATENT DOCUMENTS

| | | |
|---|---|---|
| WO | WO 1999/33982 | 7/1999 |
| WO | WO 1999/033982 A2 | 7/1999 |
| WO | WO 1999/052503 A2 | 10/1999 |
| WO | WO 2001/021810 A1 | 3/2001 |
| WO | WO 2004/058166 A2 | 7/2004 |
| WO | WO 2004/076645 A1 | 9/2004 |
| WO | WO 2005/007689 A1 | 1/2005 |
| WO | WO 2005/009346 | 2/2005 |
| WO | WO 2006/056027 A1 | 6/2006 |
| WO | WO 2006/071903 | 7/2006 |
| WO | WO 2006/095259 | 9/2006 |
| WO | WO 2007/095976 A2 | 8/2007 |
| WO | WO 2008/014979 A3 | 2/2008 |
| WO | WO 2008/052770 A2 | 5/2008 |
| WO | WO 2008/083949 A2 | 7/2008 |
| WO | WO 2009/030254 A1 | 3/2009 |
| WO | WO 2009/030481 A1 | 3/2009 |
| WO | WO 2009/095226 | 8/2009 |
| WO | WO 2009/127230 A1 | 10/2009 |
| WO | WO 2010/037408 A1 | 4/2010 |
| WO | WO 2010/037539 A1 | 4/2010 |
| WO | WO 2010/042877 A1 | 4/2010 |
| WO | WO 2010/054406 A1 | 5/2010 |
| WO | WO 2010/088927 A1 | 8/2010 |
| WO | WO 2010/115046 A2 | 10/2010 |
| WO | WO 2011/005799 A2 | 1/2011 |
| WO | WO 2011/026641 A9 | 3/2011 |
| WO | WO 2011/068810 A1 | 6/2011 |
| WO | WO 2011/069529 A1 | 6/2011 |
| WO | WO 2011/069586 A1 | 6/2011 |
| WO | WO 2011/144358 A1 | 11/2011 |
| WO | WO 2012/006369 A2 | 1/2012 |
| WO | WO 2012/006380 A2 | 1/2012 |
| WO | WO 2012/019630 A1 | 2/2012 |
| WO | WO 2012/019780 A1 | 2/2012 |
| WO | WO 2012/075040 A2 | 6/2012 |
| WO | WO 2012/089225 A1 | 7/2012 |
| WO | WO 2012/113513 A1 | 8/2012 |
| WO | WO 2012/116714 A1 | 9/2012 |
| WO | WO 2012/116715 A1 | 9/2012 |
| WO | WO 2012/116810 A1 | 9/2012 |
| WO | WO 2012/116811 A1 | 9/2012 |
| WO | WO 2013/006834 A1 | 1/2013 |
| WO | WO 2013/006837 A1 | 1/2013 |
| WO | WO 2013/006838 A1 | 1/2013 |
| WO | WO 2013/006842 A2 | 1/2013 |
| WO | WO 2013/030778 A2 | 3/2013 |
| WO | WO 2013/052167 A2 | 4/2013 |
| WO | WO 2013/055905 A1 | 4/2013 |
| WO | WO 2013/056132 A2 | 4/2013 |
| WO | WO 2013/059496 A1 | 4/2013 |
| WO | WO 2013/090186 A1 | 6/2013 |
| WO | WO 2013/090648 A1 | 6/2013 |
| WO | WO 2013/102203 A1 | 7/2013 |
| WO | WO 2013/113502 A1 | 8/2013 |
| WO | WO 2013/120497 A1 | 8/2013 |
| WO | WO 2013/120628 A1 | 8/2013 |
| WO | WO 2013/120629 A1 | 8/2013 |
| WO | WO 2013/174409 A1 | 11/2013 |
| WO | WO 2013/185069 A1 | 12/2013 |
| WO | WO 2014/071963 A1 | 5/2014 |
| WO | WO 2014/072061 A1 | 5/2014 |
| WO | WO 2014/089239 A1 | 6/2014 |
| WO | WO 2014/089486 A1 | 6/2014 |
| WO | WO 2014/127917 A1 | 8/2014 |
| WO | WO 2014/144196 A1 | 9/2014 |
| WO | WO 2014/152027 A1 | 9/2014 |
| WO | WO 2014/152774 A1 | 9/2014 |
| WO | WO 2014/152940 A1 | 9/2014 |
| WO | WO 2014/160243 A1 | 10/2014 |
| WO | WO 2015/005253 A1 | 1/2015 |
| WO | WO 2015/013551 A1 | 1/2015 |
| WO | WO 2015/024667 A1 | 2/2015 |
| WO | WO 2015/024668 A2 | 2/2015 |
| WO | WO 2015/164674 A1 | 4/2015 |
| WO | WO 2015/130584 A1 | 9/2015 |
| WO | WO 2015/134332 A2 | 9/2015 |
| WO | WO 2015/189425 A1 | 12/2015 |
| WO | WO 2016/044023 A1 | 3/2016 |
| WO | WO 2016/092460 A2 | 6/2016 |
| WO | WO 2016/116904 A1 | 7/2016 |
| WO | WO 2016/164762 A1 | 10/2016 |
| WO | WO 2016/176330 A1 | 11/2016 |
| WO | WO 2016/184822 A1 | 11/2016 |
| WO | WO 2016/201377 A1 | 12/2016 |
| WO | WO 2016/203025 A1 | 12/2016 |
| WO | WO 2017/015457 A1 | 1/2017 |
| WO | WO 2017/015463 A1 | 1/2017 |
| WO | WO 2017/020026 A1 | 2/2017 |
| WO | WO 2017/021546 A1 | 2/2017 |
| WO | WO 2017/062513 A1 | 4/2017 |
| WO | WO 2017/066789 A1 | 4/2017 |
| WO | WO 2017/070601 A1 | 4/2017 |
| WO | WO 2017/070624 A1 | 4/2017 |
| WO | WO 2017/070626 A2 | 4/2017 |
| WO | WO 2017/075531 A1 | 5/2017 |
| WO | WO 2017/109222 | 6/2017 |
| WO | WO 2017/127750 A1 | 7/2017 |
| WO | WO 2017/140905 | 8/2017 |
| WO | WO 2017/147458 | 8/2017 |
| WO | WO 2017/162265 A1 | 9/2017 |
| WO | WO 2017/165317 | 9/2017 |
| WO | WO 2017/201333 A1 | 11/2017 |
| WO | WO 2017/201340 A1 | 11/2017 |
| WO | WO 2017/201342 A1 | 11/2017 |
| WO | WO 2017/201347 A1 | 11/2017 |
| WO | WO 2017/208191 A1 | 12/2017 |
| WO | WO 2017/210215 | 12/2017 |
| WO | WO 2017/210364 A1 | 12/2017 |
| WO | WO 2018/020271 A1 | 2/2018 |
| WO | WO 2018/052549 | 3/2018 |
| WO | WO 2018/053209 A1 | 3/2018 |
| WO | WO 2018/075980 A1 | 4/2018 |
| WO | WO 2018/081459 A1 | 5/2018 |
| WO | WO 2018/081462 A1 | 5/2018 |
| WO | WO 2018/089851 A1 | 5/2018 |
| WO | WO 2018/091540 | 5/2018 |
| WO | WO 2018/107088 A1 | 6/2018 |
| WO | WO 2018/111967 A1 | 6/2018 |
| WO | WO 2018/132537 A1 | 7/2018 |
| WO | WO 2018/144082 A1 | 8/2018 |
| WO | WO 2018/144778 A1 | 8/2018 |
| WO | WO 2018/151816 A1 | 8/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/030533 A1 | 2/2021 |

(56) References Cited

FOREIGN PATENT DOCUMENTS

WO     WO 2021/050864 A1     3/2021
WO     WO 2021/055811 A1     3/2021

OTHER PUBLICATIONS

[No Author Listed], GenBank Accession No. Q5XXP3, RecName: Full=Structural polyprotein; AltName: Full=p130; Contains: RecName: Full=Capsid protein; AltName: Full=Coat protein; Short=C; Contains: RecName: Full=p62; AltName: Full=E3/E2; Contains: RecName: Full=E3 protein; AltName: Full=Spike glycoprotein E3; 2013.

Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.

Archer, Induction of a T-cell specific antigen on bone marrow lymphocytes with thymus RNA. Immunology. Jan. 1978;34(1):123-9.

Ashley et al., Bone marrow-generated dendritic cells pulsed with tumor extracts or tumor RNA induce antitumor immunity against central nervous system tumors. J Exp Med. Oct. 6, 1997;186(7):1177-82.

Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.

Bettinger et al., Peptide-mediated RNA delivery: a novel approach for enhanced transfection of primary and post-mitotic cells. Nucleic Acids Res. Sep. 15, 2001;29(18):3882-91.

Bogers et al., Potent immune responses in rhesus macaques induced by nonviral delivery of a self-amplifying RNA vaccine expressing HIV type 1 envelope with a cationic nanoemulsion. J Infect Dis. Mar. 15, 2015;211(6):947-55. doi: 10.1093/infdis/jiu522. Epub Sep. 18, 2014.

Bonehill et al., Single-step antigen loading and activation of dendritic cells by mRNA electroporation for the purpose of therapeutic vaccination in melanoma patients. Clin Cancer Res. May 2009; 15(10): 3366-3375.

Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.

Chahal et al., An RNA nanoparticle vaccine against Zika virus elicits antibody and CD8+ T cell responses in a mouse model. Sci Rep. Mar. 21, 2017;7(1):252. doi: 10.1038/s41598-017-00193-w.

Chattopadhyay et al., A chimeric vesiculo/alphavirus is an effective alphavirus vaccine. J Virol. Jan. 2013;87(1):395-402.

Cheng et al., Multifunctional triblock copolymers for intracellular messenger RNA delivery. Biomaterials. Oct. 2012; 33(28): 6868-6876.

Conry et al., Characterization of a messenger RNA polynucleotide vaccine vector. Cancer Res. Apr. 1, 1995 ;55 (7):1397-1400.

Cox et al., Predicting Zika virus structural biology: Challenges and opportunities for intervention. Antivir Chem Chemother. Aug. 2015; 24(3-4):118-26. doi: 10.1177/2040206616653873. Epub Jun. 13, 2016.

Cu et al., Enhanced Delivery and Potency of Self-Amplifying mRNA Vaccines by Electroporation in Situ, Vaccines, 2013, 1, 367-383. Abstract Only.

Dahlman et al., In vivo endothelial siRNA delivery using polymeric nanoparticles with low molecular weight. Nat Nanotechnol. Aug. 2014;9(8):648-655. doi: 10.1038/nnano.2014.84. Epub May 11, 2014.

Deering et al., Nucleic acid vaccines: prospects for non-viral delivery of mRNA vaccines. Expert Opin Drug Deliv. Jun. 2014;11(6):885-99. doi: 10.1517/17425247.2014.901308. Epub Mar. 26, 2014.

Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.

Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.

Dowd et al., Rapid development of a DNA vaccine for Zika virus. Science. Oct. 14, 2016;354(6309):237-240. Epub Sep. 22, 2016.

Durbin, Vaccine Development for Zika Virus-Timelines and Strategies. Semin Reprod Med. Sep. 2016;34(5):299-304. Epub Sep. 8, 2016.

Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.

Garcia-Arriaza et al., A novel poxvirus-based vaccine, MVA-CHIKV, is highly immunogenic and protects mice against chikungunya infection. J Virol. Mar. 2014;88(6):3527-47. doi: 10.1128/JVI.03418-13. Epub Jan. 8, 2014.

Geall et al., Nonviral delivery of self-amplifying RNA vaccines. Proc Natl Acad Sci U S A. Sep. 4, 2012;109(36):14604-9. doi:10.1073/pnas.1209367109. Epub Aug. 20, 2012.

GenBank Accession No. KJ776791, first seen on NCBI on May 12, 2014.

Gilboa et al., Cancer immunotherapy with mRNA-transfected dendritic cells. Immunol Rev. Jun. 2004;199:251-63.

Gupta et al., ZikaVR: An Integrated Zika Virus Resource for Genomics, Proteomics, Phylogenetic and Therapeutic Analysis. Sci Rep. Sep. 16, 2016;6:32713. doi: 10.1038/srep32713.

Hecker et al., Non-Viral DNA and mRNA Gene Delivery to the CNS Pre-Operatively for Neuroprotection and Following Neurotrauma. Molecular Therapy. 2004; 9, S258-S258.

Heiser et al., Induction of polyclonal prostate cancer-specific CTL using dendritic cells transfected with amplified tumor RNA. J Immunol. Mar. 1, 2001; 166(5):2953-60.

Heyes et al., Cationic lipid saturation influences intracellular delivery of encapsulated nucleic acids. J Control Release. Oct. 3, 2005;107(2):276-87.

Hoerr et al., In vivo application of RNA leads to induction of specific cytotoxic T lymphocytes and antibodies. EurJ Immunol. Jan. 2000;30(1):1-7.

Hoerr et al., Stabilized Messenger RNA (RNActiveTM) as a Tool for Innovative Gene Delivery. Tissue Engineering. Apr. 2007; 13(4): 865-925.

Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].

Holtkamp et al., Modification of antigen-encoding RNA increases stability, translational efficacy, and T-cell stimulatory capacity of dendritic cells. Blood. Dec. 15, 2006;108(13):4009-17.

Jirikowski et al., Reversal of diabetes insipidus in Brattleboro Rats: Intrahypothalamic injection of vasopressin mRNA. Science. Feb. 1992; 255(5047): 996-998.

Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.

Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.

Kanapathipillai et al., Nanoparticle targeting of anti-cancer drugs that alter intracellular signaling or influence the tumor microenvironment. Adv Drug Deliv Rev. Dec. 15, 2014;79-80:107-18. doi: 10.1016/j.addr.2014.05.005. Epub May 9, 2014.

Kariko et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.

(56) References Cited

OTHER PUBLICATIONS

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kisich et al., Antimycobacterial agent based on mRNA encoding human beta-defensin 2 enables primary macrophages to restrict growth of Mycobacterium tuberculosis.Infect Immun. Apr. 2001;69(4):2692-9.

Kofler et al., Mimicking live flavivirus immunization with a non-infectious RNA vaccine. Proc. Natl. Acad. Sci. U S A. Feb. 2004;101(7):1951-1956.

Kozielski et al., Bioreducible Cationic Polymer-Based Nanoparticles for Efficient and Environmentally Triggered Cytoplasmic siRNA Delivery to Primary Human Brain Cancer Cells, ACS Nano. Apr. 22, 2014;8(4):3232-41. doi: 10.1021/nn500704t. Epub Apr. 3, 2014.

Kreiter et al., Intranodal vaccination with naked antigen-encoding RNA elicits potent prophylactic and therapeutic antitumoral immunity. Cancer Res. 2010; 70: 9031-9040.

Kreiter et al., Tumor vaccination using messenger RNA: prospects of a future therapy. Curr Opinion in Immun. Jun. 2011; 23(3): 399-406.

Kuhn et al., mRNA as a versatile tool for exogenous protein expression. Current Gene Therapy. Oct. 2012; 12(5): 347-361.

Leitner et al., DNA and RNA-based vaccines: principles, progress and prospects. Vaccine. Dec. 10, 1999;18 (9-10):765-77.

Li et al., Overcoming obstacles to develop effective and safe siRNA therapeutics. Expert Opin Biol Ther. May 2009; 9(5): 609-19.

Lian et al., Trends and developments in liposome drug delivery systems. J Pharm Sci. Jun. 2001;90(6):667-80.

Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.

Lindgren et al., Induction of Robust B Cell Responses after Influenza mRNA Vaccination Is Accompanied by Circulating Hemagglutinin-Specific ICOS+ PD-1+ CXCR3+ T Follicular Helper Cells. Front Immunol. Nov. 13, 2017;8:1539. doi: 10.3389/fimmu.2017.01539. eCollection 2017.

Lorenzi et al., Intranasal vaccination with messenger RNA as a new approach in gene therapy: Use against tuberculosis. BMC Biotechnol. Oct. 2010; 10(77): 1-11.

Maclachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.

Madden et al., Administration of nucleoside-modifted mRNA encoding broadly neutralizing antibody protects humanized mice from HIV-1 challenge. Nat Commun. Mar. 2, 2017;8:14630. doi: 10.1038/ncomms14630. Available at https://acuitastx.com/wp-content/uploads/2015/01/Poster-Second-International-mRNA-Health-Conference.pdf.

Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.

Mahfuz Ali Khan Shaw An et al., In silico modeling and immunoinformatics probing disclose the epitope based peptide vaccine against Zika virus envelope glycoprotein. Indian J. Pharm. Biol. Res. Dec. 2014; 2(4):44-57.

Martinon et al., Induction of virus-specific cytotoxic T lymphocytes in vivo by liposome-entrapped mRNA. EurJ Immunol. Jul. 1993;23(7):1719-22.

McKenzie et al., Nucleic acid vaccines: tasks and tactics. Immunol Res. 2001;24(3):225-44.

McSweegan et al., The Global Virus Network: Challenging chikungunya. Antiviral Res. Aug. 2015;120:147-52. doi: 10.1016/j.antiviral.2015.06.003. Epub Jun. 10, 2015.

Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.

Mitchell et al., RNA transfected dendritic cells as cancer vaccines. Curr Opin Mal Ther. Apr. 2000;2(2):176-81.

Mitchell et al., RNA-transfected dendritic cells in cancer immunotherapy. J Clin Invest. Nov. 2000;106 (9):1065-9.

Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.

Muller et al., Transfection of dendritic cells with RNA induces CD4- and COB-mediated T cell immunity against breast carcinomas and reveals the immunodominance of presented T cell epitopes. J Immunol. Jun. 15, 2003;170 (12):5892-6.

Pardi et al., Zika virus protection by a single low-dose nucleoside-modified mRNA vaccination. Nature. Mar. 9, 2017;543(7644):248-251. doi: 10.1038/nature21428. Epub Feb. 2, 2017.

Parisien et al., Rationalization and prediction of selective decoding of pseudouridine-modified nonsense and sense codons. RNA. Mar. 2012;18(3):355-67. doi: 10.1261/rna.031351.111. Epub Jan. 26, 2012.

Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.

Phua et al., Messenger RNA (mRNA) nanoparticle tumour vaccination. Nanoscale. Jul. 21, 2014;6(14):7715-29. doi: 10.1039/c4nr01346h. Review.

Pollard et al., Type I IFN counteracts the induction of antigen-specific immune responses by lipid-based delivery of mRNA vaccines. Mol Ther. Jan. 2013; 21 (1): 251-259.

Pulford et al., Liposome-siRNA-peptide complexes cross the blood-brain barrier and significantly decrease PrP'C on neuronal cells and PrP'RES in infected cell cultures. PLoS One. 201 O; 5(6): e11085.

Rabinovich et al., Synthetic messenger RNA as a tool for gene therapy. Hum. Gene Ther. Oct. 2006; 17: 1027-1035.

Richner et al., Modified mRNA Vaccines Protect against Zika Virus Infection. Cell. Mar. 23, 2017;169(1):176. doi: 10.1016/j.cell.2017.03.016.

Richner et al., Vaccine Mediated Protection Against Zika Virus-Induced Congenital Disease. Cell. Jul. 13, 2017;170(2):273-283.e12. doi: 10.1016/j.cell.2017.06.040.

Rettig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.

Schirrmacher et al., Intra-pinna anti-tumor vaccination with self-replicating infectious RNA or with DNA encoding a model tumor antigen and a cytokine. Gene Ther. Jul. 2000;7(13):1137-47.

Schmitt et al., In vitro induction of a bladder cancer-specific T-cell response by mRNA-transfected dendritic cells. J Cancer Res Clin Oncol. 2001 ;127(3):203-6.

Schott et al., Viral and non-viral approaches for transient delivery of mRNA and proteins. Current Gene Ther. 2011; 11 (5): 382-398.

Segura et al., Monitoring gene therapy by external imaging of mRNA: Pilot study on murine erythropoietin. Ther Drug Monit. Oct. 2007; 29(5): 612-8.

Smits et al. RNA-based gene transfer for adult stem cells and T cells. Leukemia. 2004; 18: 1898-1902.

Sohn et al., In-vivo particle mediated delivery of mRNA to mammalian tissues: ballistic and biological effects. Wound Rep and Regen. Jul.-Aug. 2001; 287-296.

(56) References Cited

OTHER PUBLICATIONS

Strong et al., Incorporation of beta-globin untranslated regions into a Sindbis virus vector for augmentation of heterologous mRNA expression. Gene Ther. Jun. 1997;4(6):624-7.
Sullenger et al., Emerging clinical applications of RNA. Nature. Jul. 11, 2002;418(6894):252-8.
Tavernier et al., mRNA as gene therapeutic: How to control protein expression. J. of Controlled Release. Mar. 2011; 150(3): 238-247.
Tekmira, Lipid Nanoparticle-mediated delivery of messenger RNA (retrieved from the internet). Published Oct. 24, 2013. Available at http://files.shareholder.com/downloads/ABEA-50QJTB/2628241206x0x699789/47543d12-db34-4e6e-88a9-f3ae5d97b1d2/MacLachlan_mRNA_Conf_2013.pdf.
Teufel et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Vassilev et al., Microparticle-mediated RNA immunization against bovine viral diarrhea virus. Vaccine. Feb. 28, 2001;19(15-16):2012-9.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weber et al., A small antigenic determinant of the Chikungunya virus E2 protein is sufficient to induce neutralizing antibodies which are partially protective in mice. PLoS Negl Trop Dis. Apr. 23, 2015;9(4):e0003684. doi: 10.1371/journal.pntd.0003684. eCollection Apr. 2015.
Weilhammer et al., The use of nanolipoprotein particles to enhance the immunostimulatory properties of innate immune agonists against lethal influenza challenge. Biomaterials. Dec. 2013;34(38):10305-18. doi: 10.1016/j.biomaterials.2013.09.038. Epub Sep. 27, 2013.
Wong et al., An mRNA vaccine for influenza. Nat Biotechnol. Dec. 2012;30(12):1202-4. doi: 10.1038/nbt.2439.
Wong et al., An mRNA-based vaccine strategy against Zika. Cell Res. Sep. 2017;27(9):1077-1078. doi: 10.1038/cr.2017.53. Epub Apr. 11, 2017.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ying et al., Cancer therapy using a self-replicating RNA vaccine. Nat Med. Jul. 1999;5(7):823-7.
Zhou et al., RNA melanoma vaccine: induction of antitumor immunity by human glycoprotein 100 mRNA immunization. Hum Gene Ther. Nov. 1, 1999;10(16):2719-24.
Kurimoto et al., PEG-OligoRNA Hybridization of mRNA for Developing Sterically Stable Lipid Nanoparticles toward In Vivo Administration. Molecules. Apr. 3, 2019;24(7): 1303.
Poveda et al., Establishing Preferred Product Characterization for the Evaluation of RNA Vaccine Antigens. Vaccines (Basel). Sep. 27, 2019;7(4):131. doi: 10.3390/vaccines7040131.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 90/014,395, filed Oct. 24, 2019, Ciaramella et al.
U.S. Appl. No. 15/748,773, filed Jan. 30, 2018, Ciaramella et al.
U.S. Appl. No. 15/753,293, filed Feb. 17, 2018, Smith.
U.S. Appl. No. 15/753,297, filed Feb. 17, 2018, Thompson.
U.S. Appl. No. 15/748,782, filed Jan. 30, 2018, Mousavi et al.
U.S. Appl. No. 15/767,587, filed Apr. 11, 2018, Ciaramella.
U.S. Appl. No. 16/450,882, filed Jun. 24, 2019, Ciaramella.
U.S. Appl. No. 16/833,409, filed Mar. 27, 2020, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/897,859, filed Jun. 10, 2020, Ciaramella et al.
U.S. Appl. No. 16/898,268, filed Jun. 10, 2020, Ciaramella et al.
U.S. Appl. No. 15/981,762, filed May 16, 2018, Bancel et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/880,829, filed May 21, 2020, Ciaramella et al.
U.S. Appl. No. 16/897,734, filed Jun. 10, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 16/657,122, filed Oct. 18, 2019, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 16/494,162, filed Sep. 13, 2019, Ciaramella.
U.S. Appl. No. 16/494,988, filed Sep. 17, 2019, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.
U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 16/608,451, filed Oct. 25, 2019, Ciaramella et al.
U.S. Appl. No. 16/788,182, filed Feb. 11, 2020, Panther et al.
U.S. Appl. No. 16/794,318, filed Feb. 19, 2020, Mauger et al.
PCT/US2018/051120, Dec. 24, 2018, International Search Report and Written Opinion.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
Kowalski et al., Delivering the Messenger: Advances in Technologies for Therapeutic mRNA Delivery. Molecular Therapy vol. 27 No. Apr. 4, 2019.
Maier et al., Biodegradable Lipids Enabling Rapidly Eliminated Lipid Nanoparticles for Systemic Delivery of RNAi Therapeutics. Mol Ther. Aug. 2013; 21(8): 1570-1578.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Reichmuth et al., mRNA Vaccine Delivery Using Lipid Nanoparticles. Ther Deliv. 2016;7(5):319-34. doi: 10.4155/tde-2016-0006.
Sabnis et al., A Novel Amino Lipid Series for mRNA Delivery: Improved Endosomal Escape and Sustained Pharmacology and Safety in Non-human Primates. Mol Ther. Jun. 6, 2018;26(6):1509-1519. doi: 10.1016/j.ymthe.2018.03.010. Epub Mar. 14, 2018.
Schlake et al., Developing mRNA-vaccine technologies. RNA Biol. Nov. 2012;9(11):1319-30. doi: 10.4161/rna.22269. Epub Oct. 12, 2012.
Zhao et al., Nanoparticle vaccines. Vaccine. Jan. 9, 2014;32(3):327-37. doi: 10.1016/j.vaccine.2013.11.069. Epub Dec. 2, 2013.

SEQUENCE LISTING

<160> NUMBER OF SEQ ID NOS: 20

<210> SEQ ID NO 1
<211> LENGTH: 2061
<212> TYPE: RNA
<213> ORGANISM: Artificial Sequence
<220> FEATURE:
<223> OTHER INFORMATION: Synthetic Polynucleotide

<400> SEQUENCE: 1
auguggcugg ugucccuggc caucgugaca gccugugcug gcgccgcuga agugaccaga      60
agaggcagcg ccuacuacau guaccuggac cggaacgaug ccggcgaggc caucagcuuu     120

| | |
|---|---|
| ccaaccaccc ugggcaugaa caagugcuac auccagauca uggaccuggg ccacaugugc | 180 |
| gacgccacca ugagcuacga gugccccaug cuggacgagg gcguggaacc cgacgaugug | 240 |
| gacugcuggu gcaacaccac cagcaccugg gugguguacg gcaccugcua ccacaagaag | 300 |
| ggcgaagcca gacgguccag acgggccgug acacugccua gccacagcac cagaaagcug | 360 |
| cagacccggu cccagaccug gcuggaaagc agagaguaca ccaagcaccu gauccgggug | 420 |
| gaaaacugga ucuuccggaa ccccggcuuu gcccuggccg cugcugcuau ugcuuggcug | 480 |
| cugggcagca gcaccuccca gaaagugauc uaccucguga ugauccugcu gaucgcccu | 540 |
| gccuacagca uccggguguau cggcgugucc aaccgggacu ucguggaagg caugagcggc | 600 |
| ggcacauggg uggacguggu gcuggaacau ggcggcugcg ugacagugau ggcccaggac | 660 |
| aagcccaccg uggacaucga gcucgugacc accaccgugu ccaauauggc cgaagugcgg | 720 |
| agcuacugcu acgaggccag caucagcgac auggccagcg acagcagaug cccuacacag | 780 |
| ggcgaggccu accuggacaa gcaguccgac acccaguacg ugugcaagcg gacccugguc | 840 |
| gauagaggcu ggggcaaugg cugcggccug uuuggcaagg gcagccucgu gaccugcgcc | 900 |
| aaguucgccu gcagcaagaa gaugaccggc aagagcaucc agcccgagaa ccuggaauac | 960 |
| cggaucaugc ugagcgugca cggcagccag cacuccggca ugaucgugaa cgacaccggc | 1020 |
| cacgagacag acgagaaccg ggccaaggug gaaaucaccc cuaacagccc uagagccgag | 1080 |
| gccacacugg cggcuuugg aucucugggc cuggacugcg agccuagaac cggccuggau | 1140 |
| uucagcgacc uguacuaccu gaccaugaac aacaagcacu ggcuggugca aaagaguggg | 1200 |
| uuccacgaca uccccucugcc cuggcaugcc ggcgcugaua caggcacacc ccacuggaac | 1260 |
| aacaaagagg cucuggugga auucaaggac gcccacgcca gcggcagac cguggugug | 1320 |
| cugggaucuc aggaaggcgc cgugcauaca gcucuggcag cgcccugga agccaaaug | 1380 |
| gauggcgcca aaggcagacu guccagcggc caccugaagu gccggcugaa gauggacaag | 1440 |
| cugcggcuga agggcgugc cuacuccccug uguaccgccg ccuucaccuu caccaagauc | 1500 |
| cccgccgaga cacugcacgg caccgugacu ggaaguggc aguacgccgg caccgacggc | 1560 |
| ccuuguaaag ugccugcuca gauggccgug gauaugcaga cccugacccc uguggcaga | 1620 |
| cugaucaccg ccaaccccgu gaucaccgag agcaccgaga acagcaagau gaugcuggaa | 1680 |
| cuggacccac ccuucggcga cagcuacauc gugaucggcg uggagagaaa gaagaucacc | 1740 |
| caccacuggc acagaagcgg cagcaccauc ggcaaggccu uugaggcuac agugcgggga | 1800 |
| gccaagagaa uggccgugcu gggagauacc gccuggacu uggcucugu gggcggagcc | 1860 |
| cugaacucuc ugggcaaggg aauccaccag aucuucggag ccgccuuuaa gagccuguuc | 1920 |
| ggcggcauga gcugguucag ccagauccug aucggcaccc ugcugaugug gcugggccug | 1980 |
| aacaccaaga acggcagcau cucccugaug ugccuggcuc ugggaggcgu gcugaucuuc | 2040 |
| cugagcacag ccgugucugc c | 2061 |

<210

```
ccaaccaccc uggggcaugaa caagugcuac auccagauca uggaccuggg ccacaugugc      180
gacgccacca ugagcuacga gugccccaug cuggacgagg gcguggaacc cgacgaugug      240
gacugcuggu gcaacaccac cagcaccugg gugguguacg gcaccuguca ccacaagaag      300
ggcgaagcca gacgguccag acgggccgug acacugccua gccacagcac cagaaagcug      360
cagacccggu cccagaccug gcuggaaagc agagaguaca ccaagcaccu gauccggguug     420
gaaaacugga ucuuccggaa ccccggcuuu gcccuggccg cugcugcuau ugcuuggcu       480
cugggcagca gcaccuccca gaaagugauc uaccucguga ugauccugcu gaucgcccu       540
gccuacagca uccggguguau cggcguguce aaccgggacu ucguggaagg caugagcggc     600
ggcacauggg uggacguggu gcuggaacau ggcggcugcg ugacagugau ggcccaggac      660
aagcccaccg uggacaucga gcucgugacc accaccgugu ccaauauggc cgaagugcgg     720
agcuacugcu acgaggccag caucagcgac auggccagcg acagcagaug ccccagagag      780
ggcgaggccu accuggacaa gcaguccgac acccaguacg ugcaagcg acccugguug       840
gacagaggca gaggcaaugg cugcggcaga uucggcaagg gcagccucgu gaccugcgcc     900
aaguucgccu gcagcaagaa gaugaccggc aagagcaucc agcccgagaa ccuggaauac      960
cggaucaugc ugagcgugca cggcagccag cacuccggca ugaucgugaa cgacaccggc    1020
cacgagacag acgagaaccg ggccaagguug gaaaucaccc cuaacagccc uagagccgag    1080
gccacacugg gcggcuuugg aucucugggc cuggacugcg agccuagaac cggccuggau    1140
uucagcgacc uguacuaccu gaccaugaac aacaagcacu ggcuggugca caaagagugg    1200
uuccacgaca ucccucugcc cuggcaugcc ggcgcugaua caggcacacc ccacuggaac    1260
aacaaagagg cucuggugga auucaaggac gcccacgcca gcggcagac cguggugggg     1320
cugggaucuc aggaaggcgc cgugcauaca gcucuggcag gcgcccugga agccaaaaug    1380
gauggcgcca aaggcagacu guccagcggc caccugaagu gccggcugaa gauggacaag    1440
cugcggcuga agggcguguc cuaucccug uguaccgccg ccuucaccuu caccaagauc    1500
cccgccgaga cacugcacgg caccgugacu ugaagugc aguacgccgg caccgacggc    1560
ccuuguaaag ugccugcuca gauggccguga gauaugcaga cccugacccc uguggcaga    1620
cugaucaccg ccaaccccgu gaucaccgag agcaccgaga acagcaagau gaugcugagaa    1680
cuggacccac ccuuucggcga cagcuacauc gugaucggcg uggagagaaa gaagaucacc    1740
caccacuggc acagaagcgg cagcaccauc ggcaaggccu uugaggcuac agugcgggga    1800
gccaagagaa uggccgugcu gggagauacc gccgggacuu uggcucugu gggcggagcc    1860
cugaacucuc ugggcaaggg aauccaccag aucuucggag ccgccuuuaa gagccuguuc    1920
ggcggcauga gcugguucag ccagauccug aucggcaccc ugcugaugug gcugggccug    1980
aacaccaaga acggcagcau cuccccugau gccuggcuc ugggaggcgu gcugaucuuc    2040
cugagcacag ccgugucugc c                                             2061
```

<210> SEQ ID NO 3
<211> LENGTH: 2061
<212> TYPE: RNA
<213> ORGANISM: Artificial Sequence
<220> FEATURE:
<223> OTHER INFORMATION: Synthetic Polynucleotide

<400> SEQUENCE: 3
auguggcugg ugagccuggc caucgugacc gccugcgccg cgccgugga ggugaccaga      60

| | |
|---|---|
| agaggcagcg ccuacuacau guaccuggac agaagcgacg ccggcgaggc caucagcuuc | 120 |
| ccuaccaccc ugggcaugaa caagugcuac auccagauca uggaccuggg ccacaugugc | 180 |
| gacgccacca ugagcuacga gugcccuaug cuggacgagg gcguggagcc ugacgacgug | 240 |
| gacugcuggu gcaacaccac cagcaccugg guguguacg gcaccugcca ccacaagaag | 300 |
| ggagaggcga gaagaagcag gagagccgug acccugccua gccacagcac cagaaagcug | 360 |
| cagacccgga gccagaccug gcuggagagc agagaguaca ccaagcaccu gaucagagug | 420 |
| gagaacugga ucuucagaaa cccuggcuuc gcccuggccg cggcugcuau cgccuggcug | 480 |
| cugguaguu caaccagcca gaaggugauc uaccugguga ugauccugcu gaucgccccg | 540 |
| gcauacagca uccgcugcau cggcgugagc aacagagacu cguggaggg caugagcgga | 600 |
| ggaacgugg uugacguggu gcuggagcac ggcggcugcg ugaccgugau ggcccaggac | 660 |
| aagccugccg uggacaucga gcuggugacc accaccguau ccaacauggc cgaggugaga | 720 |
| agcuacugcu acgaggcuag cauaagcgac auggccagcg acagccgaug cccuacccag | 780 |
| ggagaagccu accuggacaa gcagagcgac acccaguacg ugugcaagag aacccuggug | 840 |
| gacagaggcu ggggcaacgg cugcggccug uucggcaagg gcagccuggu uacuugcgcc | 900 |
| aaguucgccu gcagcaagaa gaugaccggc aagagcaucc agccugagaa ccuggaguac | 960 |
| agaaucaugc ugagcgugca cggcagccag cacagcggca ugaucgugaa cgacaccggc | 1020 |
| cacgaaacag acgagaacag agccaaggug gagaucaccc cuaacagccc uagagccgag | 1080 |
| gccacccuug gcggcuucgg cagccucggc cuggacugcg agccuagaac gggccuggau | 1140 |
| uucagcgacc uguacuaccu gacuaugaau aacaagcacu ggcuuguuca caaggagugg | 1200 |
| uuccacgaca ucccucugcc uuggcacgcg ggagcugaca caggaaccc ucacuggaac | 1260 |
| aacaaggagg cccuaguuga guucaaggac gcccacgcca agagacagac cguggucgug | 1320 |
| cugggguccc aagagggcgc uguccacacu gcacgcugcg gcccuggaa ggccgagaug | 1380 |
| gacgcgcca agggaagacu gagcagcggc caccugaagu gcaggcugaa gauggacaag | 1440 |
| cugcggcuga agggcguguc cuacagccug ugcaccgccg ccuucaccuu caccaagauc | 1500 |
| ccugccgaga cacuacacgg cacagugacc gucgaggugc aguacgccgg caccgacggc | 1560 |
| ccuugcaagg ugccugccca gauggccguc gauaugcaaa cucugacccc uguggggacgg | 1620 |
| cuuaucaccg ccaacccugu gauuacugag agcaccgaga auagcaagau gauguuggaa | 1680 |
| cuggacccuc cuuucggcga cagcuacauc ugauggag uuggagagaa gaagaucaca | 1740 |
| caccacuggc acagaucugg aucuacuauu ggcaaggccu cgaggcaac agugagagga | 1800 |
| gcaaagagaa uggcaguucu gggagacacc gccugggauu cggaagcgu aggaggugca | 1860 |
| uugaacuccc uaggaaaggg aauccaccag aucuucggag cugcauucaa gagccuauuc | 1920 |
| ggcggaaugu ccugguucag ccagauccug aucggcaccc ugcuugugug gcuuggauug | 1980 |
| aacaccaaga acgguaguau uagcucgacc ugccuggcuc ucggcggugu gcugaucuuc | 2040 |
| cugaguacug cggugagcgc c | 2061 |

<210> SEQ ID NO 4
<211> LENGTH: 2061
<212> TYPE: RNA
<213> ORGANISM: Artificial Sequence
<220> FEATURE:
<223> OTHER INFORMATION: Synthetic Polynucleotide

<400> SEQUENCE: 4

| | |
|---|---|
| auguggcugg ugagccuggc caucgugacc gccugcgccg cgccgugga ggugaccaga | 60 |

| | |
|---|---|
| agaggcagcg ccuacuacau guaccuggac agaagcgacg ccggcgaggc caucagcuuc | 120 |
| ccuaccaccc ugggcaugaa caagugcuac auccagauca uggaccuggg ccacaugugc | 180 |
| gacgccacca ugagcuacga gugcccuaug cuggacgagg gcguggagcc ugacgacgug | 240 |
| gacugcuggu gcaacaccac cagcaccugg guggucuacg gcaccugcca ccacaagaag | 300 |
| ggcgaggcca gaagaagcag aagagccgug acccugccua gccacagcac cagaaagcug | 360 |
| cagaccagaa gccagaccug gcuggagagc agagaguaca ccaagcaccu gaucagagug | 420 |
| gagaacugga ucuucagaaa cccuggcuuc gcccuggccg ccgccgccau cgccuggcug | 480 |
| cugggcagca gcaccagcca gaaggugauc uaccuggugu gauccugcu gaucgcccu | 540 |
| gccuacagca ucagaugcau cggcgugagc aacagagacu ucguggaggg caugagcggc | 600 |
| ggcaccuggg uggacguggu gcuggagcac ggcggcugcg ugaccgugau ggcccaggac | 660 |
| aagccugccg uggacaucga gcuggugacc accaccguga gcaacauggc cgaggugaga | 720 |
| agcuacugcu acgaggccag caucagcgac auggccagcg acagcagaug cccuagagag | 780 |
| ggcgaggccu accuggacaa gcagagcgac acccaguacg ugugcaagag aacccugggug | 840 |
| gacagaggca gaggcaacgg cugcggcaga uucggcaagg gcagccuggu gaccugcgcc | 900 |
| aaguucgccu gcagcaagaa gaugaccggc aagagcaucc agccugagaa ccuggaguac | 960 |
| agaaucaugc ugagcgugca cggcagccag cacagcggca ugaucgugaa cgacaccggc | 1020 |
| cacgagaccg acgagaacag agccaaggug gagaucaccc cuaacagccc uagagccgag | 1080 |
| gccacccugg gcggcuucgg cagccugggc cuggacugcg agccuagaac cggccuggac | 1140 |
| uucagcgacc uguacuaccu gaccaugaac aacaagcacu ggcuggugca caggagugg | 1200 |
| uuccacgaca uccccucugcc uuggcacgcc ggcgccgaca ccggcacccc ucacuggaac | 1260 |
| aacaaggagg cccuggugga guucaaggac gcccacgcca agagacagac cguggugug | 1320 |
| cugggcagcc aggagggcgc cgugcacacc gcccuggccg gcgcccugga ggccgagaug | 1380 |
| gacggcgcca agggcagacu gagcagcggc caccugaagu gcagacugaa gauggacaag | 1440 |
| cugagacuga agggcgugag cuacagccug ugcaccgccg ccuucaccuu caccaagauc | 1500 |
| ccugccgaga cccugcacgg caccgugacc gguggaggug aguacgccgg caccgacggc | 1560 |
| ccuugcaagg ugccugccca gauggccgug gacaugcaga cccugacccc uguggdcaga | 1620 |
| cugaucaccg ccaacccugu gaucaccgag agcaccgaga acagcaagau gaugcuggag | 1680 |
| cuggaccucu cuuucggcga cagcuacauc gugaucggcg ugggcgagaa gaagaucacc | 1740 |
| caccacuggc acagaagcgg cagcaccauc ggcaaggccu cgaggccac cgugagaggc | 1800 |
| gccaagagaa uggccgugcu gggcgacacc gccuggacu ucggcagcgu gggcggcgcc | 1860 |
| cugaacagcc uggcaaggg cauccaccag aucuucggcg ccgccuucaa gagccuguuc | 1920 |
| ggcggcauga gcugguucag ccagauccug aucggcaccc ugcuggugug gcgggccug | 1980 |
| aacaccaaga acggcagcau cagccugacc ugccuggccc ugggcggcgu gcugaucuuc | 2040 |
| cugagcaccg ccgugagcgc c | 2061 |

<210> SEQ ID NO 5
<211> LENGTH: 2049
<212> TYPE: RNA
<213> ORGANISM: Artificial Sequence
<220> FEATURE:
<223> OTHER INFORMATION: Synthetic Polynucleotide

<400> SEQUENCE: 5

| | |
|---|---|
| auggcugg ugagccuggc caucgugaca gcgugcgcug gagccgccga gaucaccaga | 60 |
| agaggcagcg ccuacuacau guaccuggac agaagcgacg ccggcaaggc caucagcuuc | 120 |
| gccaccaccc ugggcgugaa caagugccac gugcagauca uggaccuggg ccacaugugc | 180 |
| gacgccacca ugagcuacga gugcccuaug cuggacgagg gcguggagcc ugacgacgug | 240 |
| gacugcuggu gcaacaccac cagcaccugg gugguguacg gcaccugcca ccacaagaag | 300 |
| ggcgaggcca agaagcag acgugccgug acccugccua ccacagcac cagaaagcug | 360 |
| cagaccagaa gccagaccug gcuggagagc agagaguaca ccaagcaccu gaucaaggug | 420 |
| gagaacugga ucuucagaaa cccuggcuuc gcccuggugg ccguggcaau ugccuggcug | 480 |
| cugggcagcu ccacaagcca gaaggugauc uaccuggua ugauccugcu gaucgcucca | 540 |
| gccuacagca uccgaugcau cggcgugagc aacagagacu ucguggaggg caugagcggc | 600 |
| ggaaccuggg uugacguggu gcuggagcac ggcggcugcg ugaccgugau ggcccaggac | 660 |
| aagccuaccg uggacaucga gcuggugacc accaccguua gcaacauggc cgaggugaga | 720 |
| agcuacugcu acgaggcauc caucagcgac auggccagcg acagccgcug cccuacccag | 780 |
| ggcgaagcau accucgauaa gcagagcgac acccaguacg ugugcaagag aacucucgug | 840 |
| gacagaggcu ggggcaacgg cugcggccug uucggcaagg gcagccuggu acuugcgcc | 900 |
| aaguucaccu gcagcaagaa gaugaccggc aagagcaucc agccugaaa ccuggaguac | 960 |
| agaaucaugc ugagccgugca cggcagccag cacagcggca ugaucggcua cgaaacugac | 1020 |
| gaggacagag ccaaggucga agugacccccu aacagcccua gagccgaggc cacccuugga | 1080 |
| ggcuucggcu cccucggccu ggacugcgag ccuagaacag gacucgacuu cagcgaccug | 1140 |
| uacuaccuga ccaugaacaa caagcacugg cugguccaca aggagugguu ccacgacauc | 1200 |
| ccucugccuu ggcacgccgg agcagacacc ggcacccccuc acuggaauaa caaggaggcg | 1260 |
| cuuguggagu ucaaggacgc ccacgccaag agacagaccg ugguugugcu cggaagucag | 1320 |
| gagggcgccg ugcacaccgc ccuggccgga gcccuggagg ccgagaugga cggcgcaaag | 1380 |
| ggcagacugu ucagcggcca ccugaagugc agacugaaga uggacaagcu gagacuuaag | 1440 |
| ggcgucagcu acagccugug caccgccgcc uucaccuuca ccaaggugcc ugccgaaacc | 1500 |
| cugcacggaa cuguaaccgu agaggucag uacgcaggaa ccgacggccc uugcaagauc | 1560 |
| ccugugcaga uggcggugga uaugcagacc cugacccccug uuggccguuu gaucaccgcc | 1620 |
| aacccuguga uaaccgagag caccgagaac agcaagauga ugcuggaacu ggacccuccu | 1680 |
| uucggcgaca gcuacaucgu gaucggagug ggcgauaaga agaucacccca ccacuggcau | 1740 |
| cgcagcgguu cuaccaucgg aaaggccuuc gaagcuaccg uuagaggugc aaagcgcaug | 1800 |
| gcagucuuag gugacaccgc cugggacuuc gguucugucg gaggcguguu caacagucug | 1860 |
| ggcaagggaa uccaccagau cuucggcgcu gccuucaagu cuuuguucgg agguauguc | 1920 |
| ugguucagcc agauccugau cggcacccuu cugguuggc ugggccucaa caccaagaac | 1980 |
| ggauccauau cccugaccug ccuggccuug ggcgguguca ugaucuuccu gucgacugcc | 2040 |
| gugagcgcc | 2049 |

<210> SEQ ID NO 6
<211> LENGTH: 2049
<212> TYPE: RNA
<213> ORGANISM: Artificial Sequence
<220> FEATURE:
<223> OTHER INFORMATION: Synthetic Polynucleotide

<400> SEQUENCE: 6

| | |
|---|---:|
| auguggcugg ugagccuggc caucgugacu gcuugcgcgg gugccgccga gaucaccaga | 60 |
| agaggcagcg ccuacuacau guaccuggac agaagcgacg ccggcaaggc caucagcuuc | 120 |
| gccaccaccc ugggcgugaa caagugccac gugcagauca uggaccuggg ccacaugugc | 180 |
| gacgccacca ugagcuacga gugcccuaug cuggacgagg gcguggagcc ugacgacgug | 240 |
| gacugcuggu gcaacaccac cagcaccugg ggugugacg gcaccugcca ccacaagaag | 300 |
| ggcgaggcca agaagcag gagggccgug acccugccua ccacagcac cagaaagcug | 360 |
| cagaccagaa gccagaccug gcuggagagc agagaguaca ccaagcaccu gaucaaggug | 420 |
| gagaacugga ucuucagaaa cccuggcuuc gcccuggugg ccguggcuau agccuggcug | 480 |
| cugggaucuu caacaagcca gaaggugauc uaccuggugaa ugaccugcu gaucgcgcca | 540 |
| gccuacagca uccgcugcau cggcgugagc aacagagacu ucguggaggg caugagcggc | 600 |
| ggaacuuggg uggacguggu gcuggagcac ggcggcugcg ugaccgugau ggcccaggac | 660 |
| aagccuaccg uggacaucga gcuggugacc accacgguuu cuaauauggc cgaggugaga | 720 |
| agcuacugcu acgaggcauc caucagcgac auggccagcg acagcaggug cccuagagaa | 780 |
| ggagaagccu aucucgacaa gcagagcgac acccaguacg ugugcaagag aaccccucgug | 840 |
| gacagaggca gaggcaacgg cugcggcaga uucggcaagg gcagccuggu uacgugcgcc | 900 |
| aaguucaccu gcagcaagaa gaugaccggc aagagcaucc agccugagaa ccuggaguac | 960 |
| agaaucaugc ugagcgugca cggcagccag cacagcggca ugaucggcua cgagacagac | 1020 |
| gaggacagag cuaaggucga ggugaccccu aacuccccac gcgccgaggc uacgcuggga | 1080 |
| ggcuucggau cucugggccu ggacugcgag ccuagaaccg gcuuggauuu cagcgaccug | 1140 |
| uacuaccuga ccaugaacaa caagcacugg uugguccaca aggagugguu ccacgacauc | 1200 |
| ccucugccuu ggcacgcggg cgcugacacc ggcacccccuc acuggaauaa caaggaggcc | 1260 |
| uugguggagu ucaaggacgc ccacgccaag agacagaccg uggugucuu ggguucccag | 1320 |
| gagggcgccg ugcacaccgc ccuggcagga gcucuggagg ccgagaugga cggcgccaag | 1380 |
| gguagacugu ucagcggcca ccugaagugc agacugaaga uggauaagcu gagacucaag | 1440 |
| ggugugucau acagccugug caccgccgcc uucaccuuca ccaaggugcc ugccgaaacc | 1500 |
| cugcacggaa ccgugacugu agagguacag uacgcuggca ccgacggccc uugcaagauc | 1560 |
| ccugugcaga uggccguuga caugcagacc cugaccccug ugggcaggcu gauaccgcc | 1620 |
| aacccuguga ucacugagag caccgagaac agcaagauga ugcuggaacu ggacccuccu | 1680 |
| uucggcgaca gcuacaucgu gauggcgug ggcgauaaga agaucaccca ccauuggcac | 1740 |
| agaagugguu cgacuaucgg uaaggcauuc gaagcuacag ugagaggagc caagaggaug | 1800 |
| gcagugcugg ugacaccgc cugggauuuc gguucagugg gcgcguguu caauucccug | 1860 |
| ggcaagggua uccaccagau cuucggcgcu gccuucaaga gccguucgg uggaaugagc | 1920 |
| ugguucagcc agauccugau cggcaccccuc cugguuggc uugguuugaa caccaagaac | 1980 |
| ggcucuauuu cccugaccug ccuggcacua ggaggcguca ugauauuccu gaguaccgcc | 2040 |
| gugagcgcc | 2049 |

<210> SEQ ID NO 7
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 7

```
Met Trp Leu Val Ser Leu Ala Ile Val Thr Ala Cys Ala Gly Ala Ala
1               5                   10                  15

Glu Val Thr Arg Arg Gly Ser Ala Tyr Tyr Met Tyr Leu Asp Arg Asn
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
    130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Thr Val
    210                 215                 220

Asp Ile Glu Leu Val Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Thr Gln Gly Glu Ala Tyr Leu Asp Lys Gln Ser Asp Thr Gln
            260                 265                 270

Tyr Val Cys Lys Arg Thr Leu Val Asp Arg Gly Trp Gly Asn Gly Cys
        275                 280                 285

Gly Leu Phe Gly Lys Gly Ser Leu Val Thr Cys Ala Lys Phe Ala Cys
    290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
        355                 360                 365

Leu Gly Leu Asp Cys Glu Pro Arg Thr Gly Leu Asp Phe Ser Asp Leu
    370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                405                 410                 415
```

Pro His Trp Asn Asn Lys Glu Ala Leu Val Glu Phe Lys Asp Ala His
            420                 425                 430

Ala Lys Arg Gln Thr Val Val Leu Gly Ser Gln Glu Gly Ala Val
        435                 440                 445

His Thr Ala Leu Ala Gly Ala Leu Glu Ala Glu Met Asp Gly Ala Lys
450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
            500                 505                 510

Val Gln Tyr Ala Gly Thr Asp Gly Pro Cys Lys Val Pro Ala Gln Met
        515                 520                 525

Ala Val Asp Met Gln Thr Leu Thr Pro Val Gly Arg Leu Ile Thr Ala
530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
        595                 600                 605

Asp Thr Ala Trp Asp Phe Gly Ser Val Gly Gly Ala Leu Asn Ser Leu
610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Met
                645                 650                 655

Trp Leu Gly Leu Asn Thr Lys Asn Gly Ser Ile Ser Leu Met Cys Leu
            660                 665                 670

Ala Leu Gly Gly Val Leu Ile Phe Leu Ser Thr Ala Val Ser Ala
        675                 680                 685

<210> SEQ ID NO 8
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 8

Met Trp Leu Val Ser Leu Ala Ile Val Thr Ala Cys Ala Gly Ala Ala
1               5                   10                  15

Glu Val Thr Arg Arg Gly Ser Ala Tyr Tyr Met Tyr Leu Asp Arg Asn
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

```
His His Lys Lys Gly Glu Ala Arg Arg Ser Arg Arg Ala Val Thr Leu
        100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
        130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Thr Trp Val Asp Val Val Leu
            195                 200                 205

Glu His Gly Gly Cys Val Thr Val Met Ala Gln Asp Lys Pro Thr Val
        210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Arg Glu Gly Glu Ala Tyr Leu Asp Lys Gln Ser Asp Thr Gln
            260                 265                 270

Tyr Val Cys Lys Arg Thr Leu Val Asp Arg Gly Arg Gly Asn Gly Cys
        275                 280                 285

Gly Arg Phe Gly Lys Gly Ser Leu Val Thr Cys Ala Lys Phe Ala Cys
        290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
            340                 345                 350

Thr Pro Asn Ser Pro Arg Ala Glu Ala Thr Leu Gly Gly Phe Gly Ser
        355                 360                 365

Leu Gly Leu Asp Cys Glu Pro Arg Thr Gly Leu Asp Phe Ser Asp Leu
370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                405                 410                 415

Pro His Trp Asn Asn Lys Glu Ala Leu Val Glu Phe Lys Asp Ala His
            420                 425                 430

Ala Lys Arg Gln Thr Val Val Val Leu Gly Ser Gln Glu Gly Ala Val
        435                 440                 445

His Thr Ala Leu Ala Gly Ala Leu Glu Ala Glu Met Asp Gly Ala Lys
        450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
            500                 505                 510
```

```
Val Gln Tyr Ala Gly Thr Asp Gly Pro Cys Lys Val Pro Ala Gln Met
            515                 520                 525

Ala Val Asp Met Gln Thr Leu Thr Pro Val Gly Arg Leu Ile Thr Ala
            530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                565                 570                 575

Lys Lys Ile Thr His His Trp His Arg Ser Gly Ser Thr Ile Gly Lys
            580                 585                 590

Ala Phe Glu Ala Thr Val Arg Gly Ala Lys Arg Met Ala Val Leu Gly
            595                 600                 605

Asp Thr Ala Trp Asp Phe Gly Ser Val Gly Gly Ala Leu Asn Ser Leu
            610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Met
                645                 650                 655

Trp Leu Gly Leu Asn Thr Lys Asn Gly Ser Ile Ser Leu Met Cys Leu
                660                 665                 670

Ala Leu Gly Gly Val Leu Ile Phe Leu Ser Thr Ala Val Ser Ala
            675                 680                 685

<210> SEQ ID NO 9
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 9

Met Trp Leu Val Ser Leu Ala Ile Val Thr Ala Cys Ala Gly Ala Val
1               5                   10                  15

Glu Val Thr Arg Arg Gly Ser Ala Tyr Tyr Met Tyr Leu Asp Arg Ser
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
    130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190
```

```
Asp Phe Val Glu Gly Met Ser Gly Gly Thr Trp Val Asp Val Val Leu
            195                 200                 205
Glu His Gly Gly Cys Val Thr Val Met Ala Gln Asp Lys Pro Ala Val
        210                 215                 220
Asp Ile Glu Leu Val Thr Thr Val Ser Asn Met Ala Glu Val Arg
225                 230                 235                 240
Ser Tyr Cys Tyr Glu Ala Ser Ile Ser Asp Met Ala Ser Asp Ser Arg
                245                 250                 255
Cys Pro Thr Gln Gly Glu Ala Tyr Leu Asp Lys Gln Ser Asp Thr Gln
            260                 265                 270
Tyr Val Cys Lys Arg Thr Leu Val Asp Arg Gly Trp Gly Asn Gly Cys
        275                 280                 285
Gly Leu Phe Gly Lys Gly Ser Leu Val Thr Cys Ala Lys Phe Ala Cys
    290                 295                 300
Ser Lys Lys Met Thr Gly Lys Ser Ile Gln Pro Glu Asn Leu Glu Tyr
305                 310                 315                 320
Arg Ile Met Leu Ser Val His Gly Ser Gln His Ser Gly Met Ile Val
                325                 330                 335
Asn Asp Thr Gly His Glu Thr Asp Glu Asn Arg Ala Lys Val Glu Ile
            340                 345                 350
Thr Pro Asn Ser Pro Arg Ala Glu Ala Thr Leu Gly Gly Phe Gly Ser
        355                 360                 365
Leu Gly Leu Asp Cys Glu Pro Arg Thr Gly Leu Asp Phe Ser Asp Leu
    370                 375                 380
Tyr Tyr Leu Thr Met Asn Asn Lys His Trp Leu Val His Lys Glu Trp
385                 390                 395                 400
Phe His Asp Ile Pro Leu Pro Trp His Ala Gly Ala Asp Thr Gly Thr
                405                 410                 415
Pro His Trp Asn Asn Lys Glu Ala Leu Val Glu Phe Lys Asp Ala His
            420                 425                 430
Ala Lys Arg Gln Thr Val Val Leu Gly Ser Gln Glu Gly Ala Val
        435                 440                 445
His Thr Ala Leu Ala Gly Ala Leu Glu Ala Glu Met Asp Gly Ala Lys
    450                 455                 460
Gly Arg Leu Ser Ser Gly His Leu Lys Cys Arg Leu Lys Met Asp Lys
465                 470                 475                 480
Leu Arg Leu Lys Gly Val Ser Tyr Ser Leu Cys Thr Ala Ala Phe Thr
                485                 490                 495
Phe Thr Lys Ile Pro Ala Glu Thr Leu His Gly Thr Val Thr Val Glu
            500                 505                 510
Val Gln Tyr Ala Gly Thr Asp Gly Pro Cys Lys Val Pro Ala Gln Met
        515                 520                 525
Ala Val Asp Met Gln Thr Leu Thr Pro Val Gly Arg Leu Ile Thr Ala
    530                 535                 540
Asn Pro Val Ile Thr Glu Ser Thr Glu Asn Ser Lys Met Met Leu Glu
545                 550                 555                 560
Leu Asp Pro Pro Phe Gly Asp Ser Tyr Ile Val Ile Gly Val Gly Glu
                565                 570                 575
Lys Lys Ile Thr His His Trp His Arg Ser Gly Ser Thr Ile Gly Lys
            580                 585                 590
Ala Phe Glu Ala Thr Val Arg Gly Ala Lys Arg Met Ala Val Leu Gly
        595                 600                 605
Asp Thr Ala Trp Asp Phe Gly Ser Val Gly Gly Ala Leu Asn Ser Leu
```

```
                610                 615                 620
Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Val
            645                 650                 655

Trp Leu Gly Leu Asn Thr Lys Asn Gly Ser Ile Ser Leu Thr Cys Leu
            660                 665                 670

Ala Leu Gly Gly Val Leu Ile Phe Leu Ser Thr Ala Val Ser Ala
            675                 680                 685

<210> SEQ ID NO 10
<211> LENGTH: 687
<212> TYPE: PRT
<213> ORGANISM: Artificial Sequence
<220> FEATURE:
<223> OTHER INFORMATION: Synthetic Polypeptide

<400> SEQUENCE: 10

Met Trp Leu Val Ser Leu Ala Ile Val Thr Ala Cys Ala Gly Ala Val
1               5                   10                  15

Glu Val Thr Arg Arg Gly Ser Ala Tyr Tyr Met Tyr Leu Asp Arg Ser
            20                  25                  30

Asp Ala Gly Glu Ala Ile Ser Phe Pro Thr Thr Leu Gly Met Asn Lys
        35                  40                  45

Cys Tyr Ile Gln Ile Met Asp Leu Gly His Met Cys Asp Ala Thr Met
    50                  55                  60
Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Arg Val Glu Asn Trp Ile
    130                 135                 140

Phe Arg Asn Pro Gly Phe Ala Leu Ala Ala Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Ala Val
    210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Arg Glu Gly Glu Ala Tyr Leu Asp Lys Gln Ser Asp Thr Gln
            260                 265                 270

Tyr Val Cys Lys Arg Thr Leu Val Asp Arg Gly Arg Gly Asn Gly Cys
        275                 280                 285

Gly Arg Phe Gly Lys Gly Ser Leu Val Thr Cys Ala Lys Phe Ala Cys
```

```
            290                 295                 300
Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Val
                325                 330                 335

Asn Asp Thr Gly His Glu Thr Asp Glu Asn Arg Ala Lys Val Glu Ile
                340                 345                 350

Thr Pro Asn Ser Pro Arg Ala Glu Ala Thr Leu Gly Gly Phe Gly Ser
            355                 360                 365

Leu Gly Leu Asp Cys Glu Pro Arg Thr Gly Leu Asp Phe Ser Asp Leu
        370                 375                 380

Tyr Tyr Leu Thr Met Asn Asn Lys His Trp Leu Val His Lys Glu Trp
385                 390                 395                 400

Phe His Asp Ile Pro Leu Pro Trp His Ala Gly Ala Asp Thr Gly Thr
                405                 410                 415

Pro His Trp Asn Asn Lys Glu Ala Leu Val Glu Phe Lys Asp Ala His
                420                 425                 430

Ala Lys Arg Gln Thr Val Val Val Leu Gly Ser Gln Glu Gly Ala Val
            435                 440                 445

His Thr Ala Leu Ala Gly Ala Leu Glu Ala Glu Met Asp Gly Ala Lys
        450                 455                 460

Gly Arg Leu Ser Ser Gly His Leu Lys Cys Arg Leu Lys Met Asp Lys
465                 470                 475                 480

Leu Arg Leu Lys Gly Val Ser Tyr Ser Leu Cys Thr Ala Ala Phe Thr
                485                 490                 495

Phe Thr Lys Ile Pro Ala Glu Thr Leu His Gly Thr Val Thr Val Glu
                500                 505                 510

Val Gln Tyr Ala Gly Thr Asp Gly Pro Cys Lys Val Pro Ala Gln Met
            515                 520                 525

Ala Val Asp Met Gln Thr Leu Thr Pro Val Gly Arg Leu Ile Thr Ala
        530                 535                 540

Asn Pro Val Ile Thr Glu Ser Thr Glu Asn Ser Lys Met Met Leu Glu
545                 550                 555                 560

Leu Asp Pro Pro Phe Gly Asp Ser Tyr Ile Val Ile Gly Val Gly Glu
                565                 570                 575

Lys Lys Ile Thr His His Trp His Arg Ser Gly Ser Thr Ile Gly Lys
                580                 585                 590

Ala Phe Glu Ala Thr Val Arg Gly Ala Lys Arg Met Ala Val Leu Gly
            595                 600                 605

Asp Thr Ala Trp Asp Phe Gly Ser Val Gly Gly Ala Leu Asn Ser Leu
        610                 615                 620

Gly Lys Gly Ile His Gln Ile Phe Gly Ala Ala Phe Lys Ser Leu Phe
625                 630                 635                 640

Gly Gly Met Ser Trp Phe Ser Gln Ile Leu Ile Gly Thr Leu Leu Val
                645                 650                 655

Trp Leu Gly Leu Asn Thr Lys Asn Gly Ser Ile Ser Leu Thr Cys Leu
                660                 665                 670

Ala Leu Gly Gly Val Leu Ile Phe Leu Ser Thr Ala Val Ser Ala
            675                 680                 685

<210> SEQ ID NO 11
<211> LENGTH: 683
<212> TYPE: PRT
<213> ORGANISM: Artificial Sequence
```

<220> FEATURE:
<223> OTHER INFORMATION: Synthetic Polypeptide

<400> SEQUENCE: 11

```
Met Trp Leu Val Ser Leu Ala Ile Val Thr Ala Cys Ala Gly Ala Ala
1               5                   10                  15

Glu Ile Thr Arg Arg Gly Ser Ala Tyr Tyr Met Tyr Leu Asp Arg Ser
            20                  25                  30

Asp Ala Gly Lys Ala Ile Ser Phe Ala Thr Thr Leu Gly Val Asn Lys
        35                  40                  45

Cys His Val Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
            100                 105                 110

Pro Ser His Ser Thr Arg Lys Leu Gln Thr Arg Ser Gln Thr Trp Leu
        115                 120                 125

Glu Ser Arg Glu Tyr Thr Lys His Leu Ile Lys Val Glu Asn Trp Ile
130                 135                 140

Phe Arg Asn Pro Gly Phe Ala Leu Val Ala Val Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
            180                 185                 190

Asp Phe Val Glu Gly Met Ser Gly Gly Thr Trp Val Asp Val Val Leu
        195                 200                 205

Glu His Gly Gly Cys Val Thr Val Met Ala Gln Asp Lys Pro Thr Val
    210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Thr Gln Gly Glu Ala Tyr Leu Asp Lys Gln Ser Asp Thr Gln
            260                 265                 270

Tyr Val Cys Lys Arg Thr Leu Val Asp Arg Gly Trp Gly Asn Gly Cys
        275                 280                 285

Gly Leu Phe Gly Lys Gly Ser Leu Val Thr Cys Ala Lys Phe Thr Cys
    290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Gly
                325                 330                 335

Tyr Glu Thr Asp Glu Asp Arg Ala Lys Val Glu Val Thr Pro Asn Ser
            340                 345                 350

Pro Arg Ala Glu Ala Thr Leu Gly Gly Phe Gly Ser Leu Gly Leu Asp
        355                 360                 365

Cys Glu Pro Arg Thr Gly Leu Asp Phe Ser Asp Leu Tyr Tyr Leu Thr
    370                 375                 380

Met Asn Asn Lys His Trp Leu Val His Lys Glu Trp Phe His Asp Ile
385                 390                 395                 400
```

Pro Leu Pro Trp His Ala Gly Ala Asp Thr Gly Thr Pro His Trp Asn
                405                 410                 415

Asn Lys Glu Ala Leu Val Glu Phe Lys Asp Ala His Ala Lys Arg Gln
            420                 425                 430

Thr Val Val Val Leu Gly Ser Gln Glu Gly Ala Val His Thr Ala Leu
        435                 440                 445

Ala Gly Ala Leu Glu Ala Glu Met Asp Gly Ala Lys Gly Arg Leu Phe
    450                 455                 460

Ser Gly His Leu Lys Cys Arg Leu Lys Met Asp Lys Leu Arg Leu Lys
465                 470                 475                 480

Gly Val Ser Tyr Ser Leu Cys Thr Ala Ala Phe Thr Phe Thr Lys Val
                485                 490                 495

Pro Ala Glu Thr Leu His Gly Thr Val Thr Val Glu Val Gln Tyr Ala
            500                 505                 510

Gly Thr Asp Gly Pro Cys Lys Ile Pro Val Gln Met Ala Val Asp Met
        515                 520                 525

Gln Thr Leu Thr Pro Val Gly Arg Leu Ile Thr Ala Asn Pro Val Ile
    530                 535                 540

Thr Glu Ser Thr Glu Asn Ser Lys Met Met Leu Glu Leu Asp Pro Pro
545                 550                 555                 560

Phe Gly Asp Ser Tyr Ile Val Ile Gly Val Gly Asp Lys Lys Ile Thr
                565                 570                 575

His His Trp His Arg Ser Gly Ser Thr Ile Gly Lys Ala Phe Glu Ala
            580                 585                 590

Thr Val Arg Gly Ala Lys Arg Met Ala Val Leu Gly Asp Thr Ala Trp
        595                 600                 605

Asp Phe Gly Ser Val Gly Gly Val Phe Asn Ser Leu Gly Lys Gly Ile
    610                 615                 620

His Gln Ile Phe Gly Ala Ala Phe Lys Ser Leu Phe Gly Gly Met Ser
625                 630                 635                 640

Trp Phe Ser Gln Ile Leu Ile Gly Thr Leu Leu Val Trp Leu Gly Leu
                645                 650                 655

Asn Thr Lys Asn Gly Ser Ile Ser Leu Thr Cys Leu Ala Leu Gly Gly
            660                 665                 670

Val Met Ile Phe Leu Ser Thr Ala Val Ser Ala
        675                 680

<210> SEQ ID NO 12
<211> LENGTH: 683
<212> TYPE: PRT
<213> ORGANISM: Artificial Sequence
<220> FEATURE:
<223> OTHER INFORMATION: Synthetic Polypeptide

<400> SEQUENCE: 12

Met Trp Leu Val Ser Leu Ala Ile Val Thr Ala Cys Ala Gly Ala Ala
1               5                   10                  15

Glu Ile Thr Arg Arg Gly Ser Ala Tyr Tyr Met Tyr Leu Asp Arg Ser
            20                  25                  30

Asp Ala Gly Lys Ala Ile Ser Phe Ala Thr Thr Leu Gly Val Asn Lys
        35                  40                  45

Cys His Val Gln Ile Met Asp Leu Gly His Met Cys Asp Ala Thr Met
    50                  55                  60

Ser Tyr Glu Cys Pro Met Leu Asp Glu Gly Val Glu Pro Asp Asp Val
65                  70                  75                  80

```
Asp Cys Trp Cys Asn Thr Thr Ser Thr Trp Val Val Tyr Gly Thr Cys
                85                  90                  95

His His Lys Lys Gly Glu Ala Arg Arg Ser Arg Arg Ala Val Thr Leu
                100                 105                 110

Pro Ser His Ser Thr Arg Lys Leu Gln Thr Arg Ser Gln Thr Trp Leu
                115                 120                 125

Glu Ser Arg Glu Tyr Thr Lys His Leu Ile Lys Val Glu Asn Trp Ile
        130                 135                 140

Phe Arg Asn Pro Gly Phe Ala Leu Val Ala Val Ala Ile Ala Trp Leu
145                 150                 155                 160

Leu Gly Ser Ser Thr Ser Gln Lys Val Ile Tyr Leu Val Met Ile Leu
                165                 170                 175

Leu Ile Ala Pro Ala Tyr Ser Ile Arg Cys Ile Gly Val Ser Asn Arg
                180                 185                 190

Asp Phe Val Glu Gly Met Ser Gly Gly Thr Trp Val Asp Val Val Leu
            195                 200                 205

Glu His Gly Gly Cys Val Thr Val Met Ala Gln Asp Lys Pro Thr Val
        210                 215                 220

Asp Ile Glu Leu Val Thr Thr Thr Val Ser Asn Met Ala Glu Val Arg
225                 230                 235                 240

Ser Tyr Cys Tyr Glu Ala Ser Ile Ser Asp Met Ala Ser Asp Ser Arg
                245                 250                 255

Cys Pro Arg Glu Gly Glu Ala Tyr Leu Asp Lys Gln Ser Asp Thr Gln
                260                 265                 270

Tyr Val Cys Lys Arg Thr Leu Val Asp Arg Gly Arg Gly Asn Gly Cys
                275                 280                 285

Gly Arg Phe Gly Lys Gly Ser Leu Val Thr Cys Ala Lys Phe Thr Cys
        290                 295                 300

Ser Lys Lys Met Thr Gly Lys Ser Ile Gln Pro Glu Asn Leu Glu Tyr
305                 310                 315                 320

Arg Ile Met Leu Ser Val His Gly Ser Gln His Ser Gly Met Ile Gly
                325                 330                 335

Tyr Glu Thr Asp Glu Asp Arg Ala Lys Val Glu Val Thr Pro Asn Ser
                340                 345                 350

Pro Arg Ala Glu Ala Thr Leu Gly Gly Phe Gly Ser Leu Gly Leu Asp
                355                 360                 365

Cys Glu Pro Arg Thr Gly Leu Asp Phe Ser Asp Leu Tyr Tyr Leu Thr
370                 375                 380

Met Asn Asn Lys His Trp Leu Val His Lys Glu Trp Phe His Asp Ile
385                 390                 395                 400

Pro Leu Pro Trp His Ala Gly Ala Asp Thr Gly Thr Pro His Trp Asn
                405                 410                 415

Asn Lys Glu Ala Leu Val Glu Phe Lys Asp Ala His Ala Lys Arg Gln
                420                 425                 430

Thr Val Val Val Leu Gly Ser Gln Glu Gly Ala Val His Thr Ala Leu
            435                 440                 445

Ala Gly Ala Leu Glu Ala Glu Met Asp Gly Ala Lys Gly Arg Leu Phe
        450                 455                 460

Ser Gly His Leu Lys Cys Arg Leu Lys Met Asp Lys Leu Arg Leu Lys
465                 470                 475                 480

Gly Val Ser Tyr Ser Leu Cys Thr Ala Ala Phe Thr Phe Thr Lys Val
                485                 490                 495
```

-continued

```
Pro Ala Glu Thr Leu His Gly Thr Val Thr Val Glu Val Gln Tyr Ala
                500                 505                 510
Gly Thr Asp Gly Pro Cys Lys Ile Pro Val Gln Met Ala Val Asp Met
        515                 520                 525
Gln Thr Leu Thr Pro Val Gly Arg Leu Ile Thr Ala Asn Pro Val Ile
    530                 535                 540
Thr Glu Ser Thr Glu Asn Ser Lys Met Met Leu Glu Leu Asp Pro Pro
545                 550                 555                 560
Phe Gly Asp Ser Tyr Ile Val Ile Gly Val Asp Lys Lys Ile Thr
                565                 570                 575
His His Trp His Arg Ser Gly Ser Thr Ile Gly Lys Ala Phe Glu Ala
                580                 585                 590
Thr Val Arg Gly Ala Lys Arg Met Ala Val Leu Gly Asp Thr Ala Trp
                595                 600                 605
Asp Phe Gly Ser Val Gly Gly Val Phe Asn Ser Leu Gly Lys Gly Ile
            610                 615                 620
His Gln Ile Phe Gly Ala Ala Phe Lys Ser Leu Phe Gly Gly Met Ser
625                 630                 635                 640
Trp Phe Ser Gln Ile Leu Ile Gly Thr Leu Leu Val Trp Leu Gly Leu
                645                 650                 655
Asn Thr Lys Asn Gly Ser Ile Ser Leu Thr Cys Leu Ala Leu Gly Gly
                660                 665                 670
Val Met Ile Phe Leu Ser Thr Ala Val Ser Ala
            675                 680
```

<210> SEQ ID NO 13
<211> LENGTH: 57
<212> TYPE: RNA
<213> ORGANISM: Artificial Sequence
<220> FEATURE:
<223> OTHER INFORMATION: Synthetic Polynucleotide

<400> SEQUENCE: 13
gggaauuaag agagaaaaga agaguaagaa gaaauauaag accccggcgc cgccacc    57

<210> SEQ ID NO 14
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 14
gggaauuaag agagaaaaga agaguaagaa gaaauauaag agccacc    47

<210> SEQ ID NO 15
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 15
ugauaauagg cuggagccuc gguggccuag cuucuugccc cuugggccuc ccccagccc     60 cuccucccu uccugcaccc guaccccgu ggucuuugaa uaaagucuga gugggcggc    119

<210> SEQ ID NO 16
<211> LENGTH: 119
<212> TYPE: RNA
<213> ORGANISM: Artificial Sequence

```
<220> FEATURE:
<223> OTHER INFORMATION: Synthetic Polynucleotide

<400> SEQUENCE: 16
ugauaauagg cuggagccuc gguggccaug cuucuugccc cuugggccuc cccccagccc    60
cucccucccu uccugcaccc guaccccgu ggucuuugaa uaaagucuga gugggcggc    119

<210> SEQ ID NO 17
<211> LENGTH: 690
<212> TYPE: PRT
<213> ORGANISM: Artificial Sequence
<220> FEATURE:
<223> OTHER INFORMATION: Synthetic Polypeptide

<400> SEQUENCE: 17
```

| Met | Asp | Trp | Thr | Trp | Ile | Leu | Phe | Leu | Val | Ala | Ala | Thr | Arg | Val |
|---|---|---|---|---|---|---|---|---|---|---|---|---|---|---|
| 1 | | | | 5 | | | | | 10 | | | | | 15 |

| His | Ser | Val | Glu | Val | Thr | Arg | Arg | Gly | Ser | Ala | Tyr | Tyr | Met | Tyr | Leu |
|---|---|---|---|---|---|---|---|---|---|---|---|---|---|---|---|
| | | | 20 | | | | | 25 | | | | | 30 | | |

| Asp | Arg | Ser | Asp | Ala | Gly | Glu | Ala | Ile | Ser | Phe | Pro | Thr | Thr | Leu | Gly |
|---|---|---|---|---|---|---|---|---|---|---|---|---|---|---|---|
| | | 35 | | | | | 40 | | | | | 45 | | | |

| Met | Asn | Lys | Cys | Tyr | Ile | Gln | Ile | Met | Asp | Leu | Gly | His | Met | Cys | Asp |
|---|---|---|---|---|---|---|---|---|---|---|---|---|---|---|---|
| 50 | | | | | 55 | | | | | 60 | | | | | |

| Ala | Thr | Met | Ser | Tyr | Glu | Cys | Pro | Met | Leu | Asp | Glu | Gly | Val | Glu | Pro |
|---|---|---|---|---|---|---|---|---|---|---|---|---|---|---|---|
| 65 | | | | 70 | | | | | 75 | | | | | 80 | |

| Asp | Asp | Val | Asp | Cys | Trp | Cys | Asn | Thr | Thr | Ser | Thr | Trp | Val | Val | Tyr |
|---|---|---|---|---|---|---|---|---|---|---|---|---|---|---|---|
| | | | 85 | | | | | 90 | | | | | 95 | | |

| Gly | Thr | Cys | His | His | Lys | Lys | Gly | Glu | Ala | Arg | Arg | Ser | Arg | Arg | Ala |
|---|---|---|---|---|---|---|---|---|---|---|---|---|---|---|---|
| | | 100 | | | | | 105 | | | | | 110 | | | |

| Val | Thr | Leu | Pro | Ser | His | Ser | Thr | Arg | Lys | Leu | Gln | Thr | Arg | Ser | Gln |
|---|---|---|---|---|---|---|---|---|---|---|---|---|---|---|---|
| | 115 | | | | | 120 | | | | | 125 | | | | |

| Thr | Trp | Leu | Glu | Ser | Arg | Glu | Tyr | Thr | Lys | His | Leu | Ile | Arg | Val | Glu |
|---|---|---|---|---|---|---|---|---|---|---|---|---|---|---|---|
| | 130 | | | | | 135 | | | | | 140 | | | | |

| Asn | Trp | Ile | Phe | Arg | Asn | Pro | Gly | Phe | Ala | Leu | Ala | Ala | Ala | Ala | Ile |
|---|---|---|---|---|---|---|---|---|---|---|---|---|---|---|---|
| 145 | | | | | 150 | | | | | 155 | | | | | 160 |

| Ala | Trp | Leu | Leu | Gly | Ser | Ser | Thr | Ser | Gln | Lys | Val | Ile | Tyr | Leu | Val |
|---|---|---|---|---|---|---|---|---|---|---|---|---|---|---|---|
| | | | | 165 | | | | | 170 | | | | | 175 | |

| Met | Ile | Leu | Leu | Ile | Ala | Pro | Ala | Tyr | Ser | Ile | Arg | Cys | Ile | Gly | Val |
|---|---|---|---|---|---|---|---|---|---|---|---|---|---|---|---|
| | | | 180 | | | | | 185 | | | | | 190 | | |

| Ser | Asn | Arg | Asp | Phe | Val | Glu | Gly | Met | Ser | Gly | Gly | Thr | Trp | Val | Asp |
|---|---|---|---|---|---|---|---|---|---|---|---|---|---|---|---|
| | | 195 | | | | | 200 | | | | | 205 | | | |

| Val | Val | Leu | Glu | His | Gly | Gly | Cys | Val | Thr | Val | Met | Ala | Gln | Asp | Lys |
|---|---|---|---|---|---|---|---|---|---|---|---|---|---|---|---|
| | 210 | | | | | 215 | | | | | 220 | | | | |

| Pro | Ala | Val | Asp | Ile | Glu | Leu | Val | Thr | Thr | Thr | Val | Ser | Asn | Met | Ala |
|---|---|---|---|---|---|---|---|---|---|---|---|---|---|---|---|
| 225 | | | | | 230 | | | | | 235 | | | | | 240 |

| Glu | Val | Arg | Ser | Tyr | Cys | Tyr | Glu | Ala | Ser | Ile | Ser | Asp | Met | Ala | Ser |
|---|---|---|---|---|---|---|---|---|---|---|---|---|---|---|---|
| | | | | 245 | | | | | 250 | | | | | 255 | |

| Asp | Ser | Arg | Cys | Pro | Thr | Gln | Gly | Glu | Ala | Tyr | Leu | Asp | Lys | Gln | Ser |
|---|---|---|---|---|---|---|---|---|---|---|---|---|---|---|---|
| | | | 260 | | | | | 265 | | | | | 270 | | |

| Asp | Thr | Gln | Tyr | Val | Cys | Lys | Arg | Thr | Leu | Val | Asp | Arg | Gly | Trp | Gly |
|---|---|---|---|---|---|---|---|---|---|---|---|---|---|---|---|
| | | 275 | | | | | 280 | | | | | 285 | | | |

| Asn | Gly | Cys | Gly | Leu | Phe | Gly | Lys | Gly | Ser | Leu | Val | Thr | Cys | Ala | Lys |
|---|---|---|---|---|---|---|---|---|---|---|---|---|---|---|---|
| | 290 | | | | | 295 | | | | | 300 | | | | |

| Phe | Ala | Cys | Ser | Lys | Lys | Met | Thr | Gly | Lys | Ser | Ile | Gln | Pro | Glu | Asn |
|---|---|---|---|---|---|---|---|---|---|---|---|---|---|---|---|
| 305 | | | | | 310 | | | | | 315 | | | | | 320 |

```
Leu Glu Tyr Arg Ile Met Leu Ser Val His Gly Ser Gln His Ser Gly
                325                 330                 335

Met Ile Val Asn Asp Thr Gly His Glu Thr Asp Glu Asn Arg Ala Lys
            340                 345                 350

Val Glu Ile Thr Pro Asn Ser Pro Arg Ala Glu Ala Thr Leu Gly Gly
        355                 360                 365

Phe Gly Ser Leu Gly Leu Asp Cys Glu Pro Arg Thr Gly Leu Asp Phe
    370                 375                 380

Ser Asp Leu Tyr Tyr Leu Thr Met Asn Asn Lys His Trp Leu Val His
385                 390                 395                 400

Lys Glu Trp Phe His Asp Ile Pro Leu Pro Trp His Ala Gly Ala Asp
                405                 410                 415

Thr Gly Thr Pro His Trp Asn Asn Lys Glu Ala Leu Val Glu Phe Lys
            420                 425                 430

Asp Ala His Ala Lys Arg Gln Thr Val Val Leu Gly Ser Gln Glu
        435                 440                 445

Gly Ala Val His Thr Ala Leu Ala Gly Ala Leu Glu Ala Glu Met Asp
    450                 455                 460

Gly Ala Lys Gly Arg Leu Ser Ser Gly His Leu Lys Cys Arg Leu Lys
465                 470                 475                 480

Met Asp Lys Leu Arg Leu Lys Gly Val Ser Tyr Ser Leu Cys Thr Ala
                485                 490                 495

Ala Phe Thr Phe Thr Lys Ile Pro Ala Glu Thr Leu His Gly Thr Val
            500                 505                 510

Thr Val Glu Val Gln Tyr Ala Gly Thr Asp Gly Pro Cys Lys Val Pro
        515                 520                 525

Ala Gln Met Ala Val Asp Met Gln Thr Leu Thr Pro Val Gly Arg Leu
    530                 535                 540

Ile Thr Ala Asn Pro Val Ile Thr Glu Ser Thr Glu Asn Ser Lys Met
545                 550                 555                 560

Met Leu Glu Leu Asp Pro Pro Phe Gly Asp Ser Tyr Ile Val Ile Gly
                565                 570                 575

Val Gly Glu Lys Lys Ile Thr His His Trp His Arg Ser Gly Ser Thr
            580                 585                 590

Ile Gly Lys Ala Phe Glu Ala Thr Val Arg Gly Ala Lys Arg Met Ala
        595                 600                 605

Val Leu Gly Asp Thr Ala Trp Asp Phe Gly Ser Val Gly Gly Ala Leu
    610                 615                 620

Asn Ser Leu Gly Lys Gly Ile His Gln Ile Phe Gly Ala Ala Phe Lys
625                 630                 635                 640

Ser Leu Phe Gly Gly Met Ser Trp Phe Ser Gln Ile Leu Ile Gly Thr
                645                 650                 655

Leu Leu Val Trp Leu Gly Leu Asn Thr Lys Asn Gly Ser Ile Ser Leu
            660                 665                 670

Thr Cys Leu Ala Leu Gly Gly Val Leu Ile Phe Leu Ser Thr Ala Val
        675                 680                 685

Ser Ala
    690

<210> SEQ ID NO 18
<211> LENGTH: 15
<212> TYPE: PRT
<213> ORGANISM: Artificial Sequence
<220> FEATURE:
<223> OTHER INFORMATION: Synthetic Polypeptide
```

<400> SEQUENCE: 18

Met Trp Leu Val Ser Leu Ala Ile Val Thr Ala Cys Ala Gly Ala
1               5                   10                  15

<210> SEQ ID NO 19
<211> LENGTH: 45
<212> TYPE: RNA
<213> ORGANISM: Artificial Sequence
<220> FEATURE:
<223> OTHER INFORMATION: Synthetic Polynucleotide

<400> SEQUENCE: 19
auguggcugg ugcccuggc caucgugaca gccugugcug gcgcc          45

<210> SEQ ID NO 20
<211> LENGTH: 2337
<212> TYPE: RNA
<213> ORGANISM: Artificial Sequence
<220> FEATURE:
<223> OTHER INFORMATION: Synthetic Polynucleotide

<400> SEQUENCE: 20
gggaauaaag agagaaaaga agaguaagaa gaaauauaag accccggcgc cgccaccaug      60
uggcuggugu cccuggccau cgugacagcc ugugcuggcg ccgcugaagu gaccagaaga     120
ggcagcgccu acuacaugua ccuggaccgg aacgaugccg cgaggccau cagcuuucca      180 accacccugg gcaugaacaa gugcuacauc agaucaugg accgggcca caugugcgac      240 gccaccauga gcuacgagug ccccaugcug gacgagggcu ggaacccga cgaugugac      300 ugcuggugca acaccaccag caccugggug uguacggca ccugucacca aagaagggc      360 gaagccagac ggcccagacg ggccgugaca cugccuagcc acagcaccag aaagcugcag     420 acccggucccc agaccuggcu ggaaagcaga gaguacacca agcaccugau ccggguggaa     480
aacuggaucu ccggaacccc cggcuuugcc cuggccgcug cugcuauugc uuggcugcug     540
ggcagcagca cccucccagaa agugaucuac cucgugauga uccugcugau cgccccugcc     600 uacagcauccc ggugauaucgg cguguccaac cgggacuucg uggaaggcau gagcggcggc     660
acaugggugg acguggugcu ggaacauggc ggcugcguga cagugauggc ccaggacaag     720
cccaccgugg acaucgagcu cgugaccacc accgugucca auauggccga agcgggagc      780 uacugcuacg aggccagcau cagcgacaug gccagcgaca gcagaugccc uacacagggc     840
gaggccuacc uggacaagca guccgacacc caguacgugu gcaagcggac ccuggugau      900 agaggcuggg gcaauggcug cggccuguuu ggcaagggca gccucgugac cugcgccaag     960
uucgccugca gcaagaagau gaccggcaag agcauccagc ccgagaaccu ggaauaccgg    1020
aucaugcuga gcgugcacgg cagccagcac uccggcauga ucgugaacga caccggccac    1080
gagacagacg agaaccgggc caaggugaa aucaccccua acagcccuag agccgaggcc    1140
acacugggcg gcuuuggauc ucugggcccug gacgcgagc uagaaccggc cuggauuuc    1200 agcgaccugu acuaccugac caugaacaac aagcacuggc uggugcacaa agaguguuc    1260 cacgacaucc cucugcccug gcaugccggc gcugauacag gcacaccca cuggaacaac    1320 aaagaggcuc uggugaauu caaggacgcc cacgccaagc ggcagaccgu gguggugcug    1380 ggaucuucagg aaggcgccgu gcauacagcu cuggcaggcg cccuggaagc cgaaauggau    1440
ggcgccaaag gcagacuguc cagcggccac cugaagugcc ggcugaagau ggacaagcug    1500
cggcugaagg gcgugucca cucccugugu accgccgccu ucaccuucac caagauccc    1560

```
gccgagacac ugcacggcac cgugacugug gaagugcagu acgccggcac cgacggcccu  1620
uguaaagugc cugcucagau ggccguggau augcagaccc ugaccccugu gggcagacug  1680
aucaccgcca accccgugau caccgagagc accgagaaca gcaagaugau gcuggaacug  1740
gacccacccu ucggcgacag cuacaucgug aucggcgugg gagagaagaa gaucacccac  1800
cacuggcaca gaagcggcag caccaucggc aaggccuuug aggcuacagu gcggggagcc  1860
aagagaaugg ccgugcuggg agauaccgcc ugggacuuug gcucuguggg cggagcccug  1920
aacucucugg gcaagggaau ccaccagauc uucggagccg ccuuuaagag ccuguucggc  1980
ggcaugagcu gguucagcca gauccugauc ggcacccugc ugauguggcu gggccugaac  2040
accaagaacg gcagcaucuc ccugaugugc cuggcucugg gaggcgugcu gaucuuccug  2100
agcacagccg ugucugccug auaauaggcu ggagccucgg uggccuagcu ucuugccccu  2160
ugggccuccc cccagcsccu ccuccccuuc cugcacccgu accccgugg ucuuugaaua  2220 aagucugagu gggcggcaaa aaaaaaaaaa aaaaaaaaa aaaaaaaaaa aaaaaaaaaa  2280
aaaaaaaaaa aaaaaaaaaa aaaaaaaaaa aaaaaaaaaa aaaaaaaaaa aaaaaaa     2337
```

ZIKA VIRUS MRNA VACCINES

RELATED APPLICATIONS

This application is a division of U.S. application Ser. No. 16/131,793, filed Sep. 14, 2018, which claims the benefit under 35 U.S.C. § 119(e) of U.S. provisional application No. 62/558,746, filed Sep. 14, 2017, each of which is incorporated by reference herein in its entirety.

GOVERNMENT LICENSE RIGHTS

This invention was made with government support under Contract No. W911NF-13-1-0417 awarded by Defense Advanced Research Projects Agency (DARPA). The government has certain rights in the invention.

BACKGROUND

Zika virus (ZIKV) was identified in 1947 from a sentinel Rhesus monkey in the Zika Forest of Uganda. Historically, ZIKV circulated between *Aedes* species mosquitoes, non-human primates in the jungle, and episodically spilled into human populations in Africa and parts of Southeast Asia. Infection was associated with a mild, self-limiting febrile illness characterized by headache, rash, conjunctivitis, myalgia, and arthralgia. Since 2010, and especially in the context of its spread and dissemination to countries of the Western Hemisphere, more severe clinical consequences have been observed. Infection of fetuses in utero during pregnancy, particularly during the first and second trimesters, has been associated with placental insufficiency and congenital malformations including cerebral calcifications, microcephaly, and miscarriage. In adults, ZIKV infection is linked to an increased incidence of Guillain-Barré-syndrome (GBS), an autoimmune disease characterized by paralysis and polyneuropathy. In addition to mosquito and in utero transmission, sexual transmission of ZIKV has been described from men-to-women, men-to-men, and women-to-men. Persistent ZIKV infection can occur, as viral RNA has been detected in semen, sperm, and vaginal secretions up to 6 months following infection. Thus, ZIKV is now a global disease with locally-acquired and travel-associated transmission through multiple routes in the Americas, Africa, and Asia. The emergence of ZIKV infection has prompted a global effort to develop safe and effective vaccines.

SUMMARY

Experimental results provided herein demonstrate an unexpected improvement in efficacy with Zika virus (ZIKV) RNA vaccines encoding a Japanese encephalitis virus (JEV) signal peptide fused to a ZIKV prME protein. As shown in the Examples, the ZIKV mRNA vaccine encoding a JEV signal peptide fused to prME unexpectedly provided sterilizing immunity in non-human primates at a 20-fold lower dose relative to a ZIKV mRNA vaccine encoding a IgE signal peptide fused to prME.

Thus, in some aspects, provided herein are RNA vaccines that comprise a 5' UTR, an ORF encoding a JEV signal peptide fused to a ZIKV prME protein, and a 3' UTR. In some embodiments, the 5' UTR is selected from SEQ ID NO:13 and SEQ ID NO:14. In some embodiments, the ORF comprises a sequence selected from SEQ ID NOs:1-6. In some embodiments, the 3' UTR is selected from SEQ ID NO:15 and SEQ ID NO:16. In some embodiments, the JEV signal peptide comprises the following sequence: MWLVSLAIVTACAGA (SEQ ID NO:18). In some embodiments, the JEV signal peptide is encoded by the following sequence: AUGUGGCUGGUGUCCCUGGC-CAUCGUGACA GCCUGUGCUGGCGCC (SEQ ID NO:19).

Also provided herein are methods comprising administering to a subject a RNA vaccine comprising an open reading frame (ORF) encoding a JEV signal peptide fused to a ZIKV prME protein in an effective amount to induce in the subject a ZIKV prME-specific immune response, wherein the effective amount is sufficient to provide sterilizing immunity in the subject at an at least 10-fold lower dose relative to a ZIKV mRNA vaccine encoding a IgE signal peptide fused to prME. In some embodiments, the effective amount is sufficient to provide sterilizing immunity in the subject at an at least 20-fold lower dose relative to a ZIKV mRNA vaccine encoding a IgE signal peptide fused to prME.

In some aspects, the methods comprise administering to a subject a RNA vaccine comprising an ORF encoding a JEV signal peptide fused to a ZIKV prME protein in an effective amount to reduce viral load in the subject by at least 80%, relative to a control, at 3-7 days following exposure to ZIKV, wherein the control is the viral load in a subject administered a ZIKV RNA vaccine lacking the JEV signal sequence.

In other aspects, the methods comprise administering to a subject a RNA vaccine comprising an ORF encoding a JEV signal peptide fused to a ZIKV prME protein in an effective amount to induce in the subject a ZIKV prME-specific immune response, wherein efficacy of the RNA vaccine is at least 80% relative to unvaccinated control subjects.

DETAILED DESCRIPTION

Figure 1:
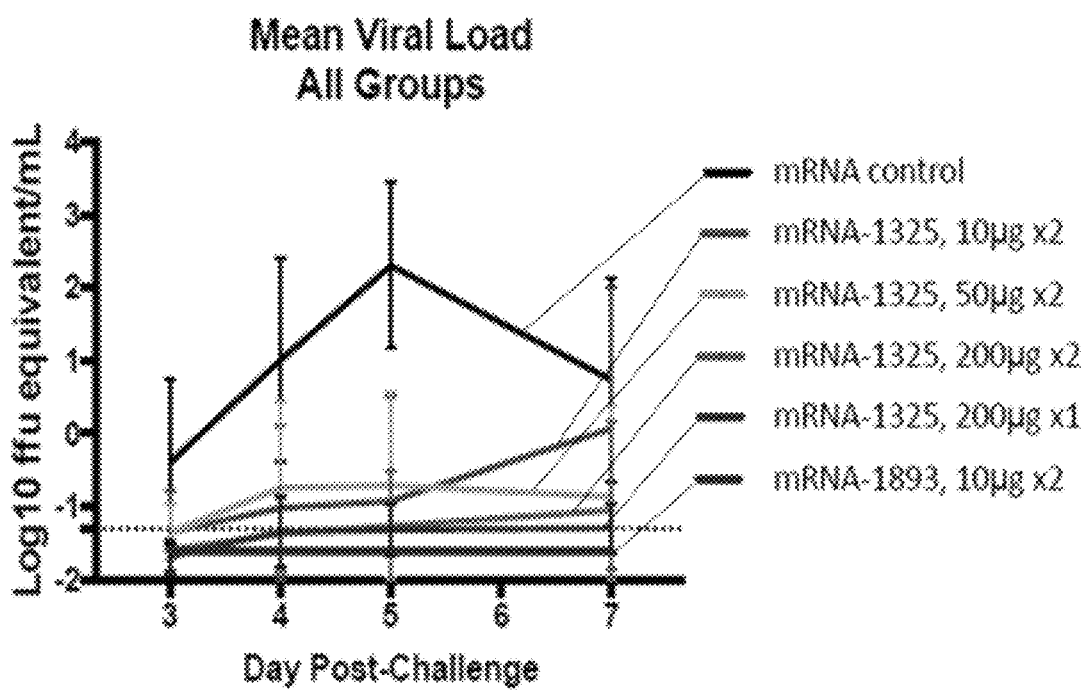
FIG. 1 is a graph showing the viral yield ($\log_{10}$ focus forming units (FFU)/ml) 3, 4, 5, 6 and 7 days post challenge (with ZIKV) in non-human primates (NHPs) vaccinated with 10 µg, 50 µg, or 200 µg ZIKV mRNA vaccine. Vaccine 'mRNA-1325' encodes an IgE signal peptide fused to ZIKV prME. Vaccine 'mRNA-1893' encodes a JEV signal peptide fused to ZIKV prME. A single 200 µg dose of the mRNA-1325 vaccine confers nearly complete protection. Unexpectedly, the mRNA-1893 vaccine outperforms the mRNA-1325 vaccine in this model by at least 20×.

Zika virus (ZIKV) is a member of the Flaviviridae virus family and the flavivirus genus. In humans, it causes a disease known as Zika fever. It is related to dengue, yellow fever, West Nile and Japanese encephalitis, viruses that are also members of the virus family Flaviviridae. ZIKV is spread to people through mosquito bites. The most common symptoms of ZIKV disease (Zika) are fever, rash, joint pain, and red eye. The illness is usually mild with symptoms lasting from several days to a week. There is no vaccine to prevent, or medicine to treat ZIKV.

Provided herein, in some embodiments, are ZIKV ribonucleic acid (RNA) vaccines (e.g., mRNA vaccines) comprising a 5' untranslated region (UTR), an open reading frame (ORF) encoding a JEV signal peptide fused to a ZIKV prME protein, and a 3' UTR. In some embodiments, the ZIKV RNA vaccines comprise a polyA tail.

A 5' UTR is region of an mRNA that is directly upstream (5') from the start codon (the first codon of an mRNA transcript translated by a ribosome). A 5' UTR does not encode a polypeptide (is non-coding). In some embodiments, a 5' UTR of the present disclosure comprises a sequence selected from SEQ ID NO:13 and SEQ ID NO:14.

A 3' UTR is region of an mRNA that is directly downstream (3') from the stop codon (the codon of an mRNA transcript that signals a termination of translation) A 3' UTR does not encode a polypeptide (is non-coding). In some embodiments, a 3' UTR of the present disclosure comprises a sequence selected from SEQ ID NO:15 and SEQ ID NO:16.

A polyA tail is a region of mRNA that is downstream, e.g., directly downstream, from the 3' UTR and contains multiple, consecutive adenosine monophosphates. In a relevant biological setting (e.g., in cells, in vivo), the polyA tail functions to protect mRNA from enzymatic degradation, e.g., in the cytoplasm, and aids in transcription termination, export of the mRNA from the nucleus, and translation. A polyA tail may comprise, for example, 10 to 300 adenosine monophosphates. For example, a polyA tail may comprise 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail comprises 50 to 250 adenosine monophosphates. In some embodiments, a polyA tail comprises 100 adenosine monophosphates.

In some embodiments, the ZIKV RNA vaccine comprises 5' terminal cap, for example, 7mG(5')ppp(5')NlmpNp.

An open reading frame is a continuous stretch of DNA or RNA beginning with a start codon (e.g., methionine (ATG or AUG)) and ending with a stop codon (e.g., TAA, TAG or TGA, or UAA, UAG or UGA). In some embodiments, an ORF of the present disclosure is selected from SEQ ID NO:1, SEQ ID NO:2, SEQ ID NO:3, SEQ ID NO:4, SEQ ID NO:5, and SEQ ID NO:6. In some embodiments, the ORF comprises the sequence of SEQ ID NO:1. In some embodiments, the ORF comprises the sequence of SEQ ID NO:2. In some embodiments, the ORF comprises the sequence of SEQ ID NO:3. In some embodiments, the ORF comprises the sequence of SEQ ID NO:4. In some embodiments, the ORF comprises the sequence of SEQ ID NO:5. In some embodiments, the ORF comprises the sequence of SEQ ID NO:6.

The ZIKV RNA vaccines (e.g., mRNA vaccines) of the present disclosure encode a JEV signal peptide (e.g., SEQ ID NO:18) fused (in frame) to a ZIKV prME protein. The particular prME sequence may be from any ZIKV strain, for example those strains as are known in the art or as otherwise described herein, such as a Brazilian strain, a Micronesian strain, or an African strain. Within the Zika family, there is a high level of homology within the prME sequence (>90%) across all strains so far isolated. The high degree of homology is also preserved when comparing the original isolates from 1947 to the more contemporary strains circulating in Brazil in 2015, suggesting that there is "drift" occurring from the original isolates. Furthermore, attenuated virus preparations have provided cross-immunization to all other strains tested, including Latin American/Asian, and African. Overall, this data suggests that cross-protection of all Zika strains is possible with a vaccine based on prME. In fact, the prM/M and E proteins of ZIKV have a very high level (99%) of sequence conservation between the currently circulating Asiatic and Brazilian viral strains.

The M and E proteins are on the surface of the viral particle. Neutralizing antibodies predominantly bind to the E protein, the preM/M protein functions as a chaperone for proper folding of E protein and prevent premature fusion of E protein within acidic compartments along the cellular secretory pathway.

In some embodiments, the ZIKV prME protein comprises a sequence selected from SEQ ID NO:7, SEQ ID NO:8, SEQ ID NO:9, SEQ ID NO:10, SEQ ID NO:11, and SEQ ID NO:12. In some embodiments, the ZIKV prME protein comprises the sequence of SEQ ID NO:7. In some embodiments, the ZIKV prME protein comprises the sequence of SEQ ID NO:8. In some embodiments, the ZIKV prME protein comprises the sequence of SEQ ID NO:9. In some embodiments, the ZIKV prME protein comprises the sequence of SEQ ID NO:10. In some embodiments, the ZIKV prME protein comprises the sequence of SEQ ID NO:11. In some embodiments, the ZIKV prME protein comprises the sequence of SEQ ID NO:12.

ZIKV RNA vaccines (e.g., mRNA vaccines) of the present disclosure encode a JEV signal peptide fused to a prME protein. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane. In some embodiments, the JEV signal peptide of the present disclosure comprises the sequence of SEQ ID NO:18.

In some embodiments, a RNA (e.g., mRNA) of a ZIKV RNA vaccine of the present disclosure is chemically modified. For example, at least 80% of the uracil in the ORF may have a chemical modification selected from N1-methyl-pseudouridine and N1-ethyl-pseudouridine. In some embodiments, at least 85%, at least 90%, at least 95% or 100% of the uracil in the ORF have a chemical modification. In some embodiments, the chemical modification is in the 5-position of the uracil.

In some embodiments, at least one RNA (e.g., mRNA) of the ZIKV RNA vaccines of the present disclosure are not chemically modified, and comprise the standard ribonucleotides consisting of adenosine, guanosine, cytosine and uridine.

ZIKV RNA vaccines (e.g., mRNA vaccines) of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid. In some embodiments, the lipid nanoparticle comprises a molar ratio of 20-60% ionizable cationic lipid, 5-25% non-cationic lipid, 25-55% sterol, and 0.5-15% PEG-modified lipid. In some embodiments, the ionizable cationic lipid comprises the following compound:

Data provided herein demonstrates that ZIKV mRNA vaccines encoding a JEV signal peptide fused to prME provide sterilizing immunity in non-human primates at a 20-fold lower dose relative to a ZIKV mRNA vaccine encoding a IgE signal peptide fused to prME. Thus, provided herein, in some embodiments, are methods comprising administering to a subject a RNA vaccine comprising an ORF encoding a JEV signal peptide fused to a ZIKV prME protein in an effective amount to induce in the subject a ZIKV prME-specific immune response, wherein the effective amount is sufficient to provide sterilizing immunity in the subject at an at least 5-fold lower dose relative to a ZIKV mRNA vaccine encoding a IgE signal peptide fused to prME. In some embodiments, the effective amount is sufficient to provide sterilizing immunity in the subject at an at least 10-fold lower dose relative to a ZIKV mRNA vaccine encoding a IgE signal peptide fused to prME. the effective amount is sufficient to provide sterilizing immunity in the subject at an at least 15-fold lower dose relative to a ZIKV mRNA vaccine encoding a IgE signal peptide fused to prME. the effective amount is sufficient to provide sterilizing immunity in the subject at an at least 20-fold lower dose relative to a ZIKV mRNA vaccine encoding a IgE signal peptide fused to prME.

A subject may be any mammal, including non-human primate and human subjects. Typically, a subject is a human subject.

In some embodiments, methods of the present disclosure comprise administering to a subject a RNA vaccine comprising an ORF encoding a JEV signal peptide fused to a ZIKV prME protein in an effective amount to reduce viral load in the subject by at least 80%, relative to a control (e.g., at 3-7 days following exposure to ZIKV), wherein the control is the viral load in a subject administered a ZIKV RNA vaccine lacking the JEV signal sequence. In some embodiments, the amount of ZIKV RNA vaccine administered is effective to reduce viral load in the subject by at least 85%, at least 90%, at least 95%, at least 98% or 100%. In some embodiments, the control is the viral load in a subject administered a ZIKV RNA vaccine containing an IgE signal sequence. In some embodiments, the control is the viral load in an unvaccinated subject.

In some embodiments, the methods comprise administering to a subject ZIKV vaccine comprising an ORF encoding a JEV signal peptide fused to a ZIKV prME protein in an effective amount to induce in the subject a ZIKV prME-specific immune response, wherein efficacy of the RNA vaccine is at least 60% relative to unvaccinated control subjects. For example, the efficacy of the ZIKV RNA vaccine may be at least 65%, at least 70%, at least 75%, at least 80%, at least 85%, at least 90%, or at least 98%, relative to unvaccinated control subjects. In some embodiments, the efficacy of the RNA vaccine is at least 80% relative to unvaccinated control subjects. In some embodiments, the efficacy of the RNA vaccine is at least 95% relative to unvaccinated control subjects.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

Efficacy=(ARU−ARV)/ARU×100; and

Efficacy=(1−RR)×100.

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

Effectiveness=(1−OR)×100.

In some embodiments, the effective amount of a ZIKV RNA vaccine is sufficient to produce detectable levels of ZIKV prME protein as measured in serum of the subject at 1-72 hours post administration.

In some embodiments, the effective amount of a ZIKV RNA vaccine amount is sufficient to produce a 1,000-10,000 neutralization titer produced by neutralizing antibody against the ZIKV prME protein as measured in serum of the subject at 1-72 hours post administration. In some embodiments, the effective amount of a ZIKV RNA vaccine amount is sufficient to produce a 1,000-5,000 neutralization titer produced by neutralizing antibody against the ZIKV prME protein as measured in serum of the subject at 1-72 hours post administration. In some embodiments, the effective amount of a ZIKV RNA vaccine amount is sufficient to produce a 5,000-10,000 neutralization titer produced by neutralizing antibody against the ZIKV prME protein as measured in serum of the subject at 1-72 hours post administration.

In some embodiments, an anti-ZIKV prME protein antibody titer produced in a subject administered a ZIKV RNA vaccine is increased by at least 1 log relative to a control, wherein the control is an anti-ZIKV prME protein antibody titer produced in a subject who has not been administered a vaccine against ZIKV. In some embodiments, an anti-ZIKV prME protein antibody titer produced in a subject administered a ZIKV RNA vaccine is increased by at least 2 log relative to the control. In some embodiments, an anti-ZIKV prME protein antibody titer produced in a subject administered a ZIKV RNA vaccine is increased by at least 5 log relative to the control. In some embodiments, an anti-ZIKV prME protein antibody titer produced in a subject administered a ZIKV RNA vaccine is increased by at least 10 log relative to the control.

In some embodiments, an anti-ZIKV prME protein antibody titer produced in a subject is increased at least 2 times relative to a control, wherein the control is an anti-ZIKV prME protein antibody titer produced in a subject who has not been administered a vaccine against ZIKV. In some embodiments, an anti-ZIKV prME protein antibody titer produced in a subject is increased at least 5 times relative to a control. In some embodiments, an anti-ZIKV prME protein antibody titer produced in a subject is increased at least 10 times relative to a control.

The effective amount of a ZIKV RNA vaccine (e.g., mRNA vaccine), as provided herein, surprisingly may be as low as 20 µg, administered for example as a single dose or as two 10 µg doses. In some embodiments, the effective amount is 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 110 µg, 120 µg, 130 µg, 140 µg, 150 µg, 160 µg, 170 µg, 180 µg, 190 µg or 200 µg. In some embodiments, the effective amount is a total dose of 25 µg-200 µg.

Table 1 below provides examples of ZIKV mRNA vaccine sequences and corresponding protein sequences encoded by the vaccines.

TABLE 1

| ZIKV mRNA Vaccine Sequences | |
|---|---|
| ORF (with JEV signal sequence underlined) | Protein (with JEV signal sequence underlined) |
| ZIKV prME Brazil Isolate (mRNA) <u>AUGUGGCUGGUGUCCCUGGCCAUCGUGACA GCCUGUGCUGGCGCCGCUGAAGUGACCAGA</u> AGAGGCAGCGCCUACUACAUGUACCUGGAC CGGAACGAUGCCGGCGAGGCCAUCAGCUUU CCAACCACCCUGGGCAUGAACAAGUGCUAC AUCCAGAUCAUGGACCUGGGCCACAUGUGC GACGCCACCAUGAGCUACGAGUGCCCCAUG CUGGACGAGGGCGUGGAACCCGACGAUGUG GACUGCUGGUGCAACACCACCAGCACCUGG GUGGUGUACGGCACCUGUCACCACAAGAAG GGCGAAGCCAGACGGUCCAGACGGGCCGUG ACACUGCCUAGCCACAGCACCAGAAAGCUG CAGACCCGGUCCCAGACCUGGCUGGAAAGC AGAGAGUACACCAAGCACCUGAUCCGGGUG GAAAACUGGAUCUUCCGGAACCCCGGCUUU GCCCUGGCCGCUGCUGCUAUUGCUUGGCUG CUGGGCAGCAGCACCUCCCAGAAAGUGAUC UACCUCGUGAUGAUCCUGCUGAUCGCCCCU GCCUACAGCAUCCGGUGUAUCGGCGUGUCC AACCGGGACUUCGUGGAAGGCAUGAGCGGC GGCACAUGGGUGGACGUGGUGCUGGAACAU GGCGGCUGCGUGACAGUGAUGGCCCAGGAC AAGCCCACCGUGGACAUCGAGCUCGUGACC ACCACCGUGUCCAAUAUGGCCGAAGUGCGG AGCUACUGCUACGAGGCCAGCAUCAGCGAC AUGGCCAGCGACAGCAGAUGCCCUACACAG GGCGAGGCCUACCUGGACAAGCAGUCCGAC ACCCAGUACGUGUGCAAGCGGACCCUGGUG GAUAGAGGCUGGGGCAAUGGCUGCGGCCUG UUUGGCAAGGGCAGCCUCGUGACCUGCGCC AAGUUCGCCUGCAGCAAGAAGAUGACCGGC AAGAGCAUCCAGCCCGAGAACCUGGAAUAC CGGAUCAUGCUGAGCGUGCACGGCAGCCAG CACUCCGGCAUGAUCGUGAACGACACCGGC CACGAGACAGACGAGAACCGGGCCAAGGUG GAAAUCACCCCUAACAGCCCUAGAGCCGAG GCCACACUGGGCGGCUUUGGAUCUCUGGGC CUGGACUGCGAGCCUAGAACCGGCCUGGAU UUCAGCGACCUGUACUACCUGACCAUGAAC AACAAGCACUGGCUGGUGCACAAAGAGUGG UUCCACGACAUCCCUCUGCCCUGGCAUGCC GGCGCUGAUACAGGCACACCCCACUGGAAC AACAAAGAGGCUCUGGUGGAAUUCAAGGAC GCCCACGCCAAGCGGCAGACCGUGGUGGUG CUGGGAUCUCAGGAAGGCGCCGUGCAUACA GCUCUGGCAGGCGCCCUGGAAGCCGAAAUG GAUGGCGCCAAAGGCAGACUGUCCAGCGGC CACCUGAAGUGCCGGCUGAAGAUGGACAAG CUGCGGCUGAAGGGCGUGUCCUACUCCCUG UGUACCGCCGCCUUCACCUUCACCAAGAUC CCCGCCGAGACACUGCACGGCACCGUGACU GUGGAAGUGCAGUACGCCGGCACCGACGGC CCUUGUAAAGUGCCUGCUCAGAUGGCCGUG GAUAUGCAGACCCUGACCCCUGUGGGCAGA CUGAUCACCGCCAACCCCGUGAUCACCGAG AGCACCGAGAACAGCAAGAUGAUGCUGGAA CUGGACCCACCCUUCGGCGACAGCUACAUC GUGAUCGGCGUGGGAGAGAAGAAGAUCACC CACCACUGGCACAGAAGCGGCAGCACCAUC | ZIKV prME Brazil Isolate (protein) <u>MWLVSLAIVTACAGAAEVTRRGSAYYMYLDR</u> NDAGEAISFPTTLGMNKCYIQIMDLGHMCDA TMSYECPMLDEGVEPDDVDCWCNTTSTWVVY GTCHHKKGEARRSRRAVTLPSHSTRKLQTRS QTWLESREYTKHLIRVENWIFRNPGFALAAA AIAWLLGSSTSQKVIYLVMILLIAPAYSIRC IGVSNRDFVEGMSGGTWVDVVLEHGGCVTVM AQDKPTVDIELVTTTVSNMAEVRSYCYEASI SDMASDSRCPTQGEAYLDKQSDTQYVCKRTL VDRGWGNGCGLFGKGSLVTCAKFACSKKMTG KSIQPENLEYRIMLSVHGSQHSGMIVNDTGH ETDENRAKVEITPNSPRAEATLGGFGSLGLD CEPRTGLDFSDLYYLTMNNKHWLVHKEWFHD IPLPWHAGADTGTPHWNNKEALVEFKDAHAK RQTVVVLGSQEGAVHTALAGALEAEMDGAKG RLSSGHLKCRLKMDKLRLKGVSYSLCTAAFT FTKIPAETLHGTVTVEVQYAGTDGPCKVPAQ MAVDMQTLTPVGRLITANPVITESTENSKMM LELDPPFGDSYIVIGVGEKKITHHWHRSGST IGKAFEATVRGAKRMAVLGDTAWDFGSVGGA LNSLGKGIHQIFGAAFKSLFGGMSWFSQILI GTLLMWLGLNTKNGSISLMCLALGGVLIFLS TAVSA (SEQ ID NO: 7) |

TABLE 1-continued

ZIKV mRNA Vaccine Sequences

| ORF (with JEV signal sequence underlined) | Protein (with JEV signal sequence underlined) |
|---|---|
| GGCAAGGCCUUUGAGGCUACAGUGCGGGGA GCCAAGAGAAUGGCCGUGCUGGGAGAUACC GCCUGGGACUUUGGCUCUGUGGGCGGAGCC CUGAACUCUCUGGGCAAGGGAAUCCACCAG AUCUUCGGAGCCGCCUUUAAGAGCCUGUUC GGCGGCAUGAGCUGGUUCAGCCAGAUCCUG AUCGGCACCCUGCUGAUGUGGCUGGGCCUG AACACCAAGAACGGCAGCAUCUCCCUGAUG UGCCUGGCUCUGGGGAGGCGUGCUGAUCUUC CUGAGCACAGCCGUGUCUGCC (SEQ ID NO: 1) | |
| ZIKV prME Brazil Isolate (mRNA), with T76R, Q77E, W101R, L107R mutations <u>AUGUGGCUGGUGUCCCUGGCCAUCGUGACA GCCUGUGCUGGCGCCG</u>CUGAAGUGACCAGA AGAGGCAGCGCCUACUACAUGUACCUGGAC CGGAACGAUGCCGGCGAGGCCAUCAGCUUU CCAACCACCCUGGGCAUGAACAAGUGCUAC AUCCAGAUCAUGGACCUGGGCCACAUGUGC GACGCCACCAUGAGCUACGAGUGCCCCAUG CUGGACGAGGGCGUGGAACCCGACGAUGUG GACUGCUGGUGCAACACCAGCACCUGG GUGGUGUACGGCACCUGUCACCACAAGAAG GGCGAAGCCAGACGGUCCAGACGGGCCGUG ACACUGCCUAGCCACAGCACCAGAAAGCUG CAGACCCGGUCCCAGACCUGGCUGGAAAGC AGAGAGUACACCAAGCACCUGAUCCGGGUG GAAAACUGGAUCUUCCGGAACCCCGGCUUU GCCCUGGCCGCUGCUGCUAUUGCUUGGCUG CUGGGCAGCAGCACCUCCCAGAAAGUGAUC UACCUCGUGAUGAUCCUGCUGAUCGCCCCU GCCUACAGCAUCCGGUGUAUCGGCGUGUCC AACCGGGACUUCGUGGAAGGCAUGAGCGGC GGCACAUGGGUGGACGUGGUGCUGGAACAU GGCGGCUGCGUGACAGUGAUGGCCCAGGAC AAGCCCACCGUGGACAUCGAGCUCGUGACC ACCACCGUGUCCAAUAUGGCCGAAGUGCGG AGCUACUGCUACGAGGCCAGCAUCAGCGAC AUGGCCAGCGACAGCAGAUGCCCCAGAGAG GGCGAGGCCUACCUGGACAAGCAGUCCGAC ACCCAGUACGUGUGCAAGCGGACCCUGGUG GACAGAGGCAGAGGCAAUGGCUGCGGCAGA UUCGGCAAGGGCAGCCUCGUGACCUGCGCC AAGUUCGCCUGCAGCAAGAAGAUGACCGGC AAGAGCAUCCAGCCCGAGAACCUGGAAUAC CGGAUCAUGCUGAGCGUGCACGGCAGCCAG CACUCCGGCAUGAUCGUGAACGACACCGGC CACGAGACAGACGAGAACCGGGCCAAGGUG GAAAUCACCCCUAACAGCCCUAGAGCCGAG GCCACACUGGGCGGCUUUGGAUCUCUGGGC CUGGACUGCGAGCCUAGAACCGGCCUGGAU UUCAGCGACCUGUACUACCUGACCAUGAAC AACAAGCACUGGCUGGUGCACAAAGAGUGG UUCCACGACAUCCCUCUGCCCUGGCAUGCC GGCGCUGAUACAGGCACACCCCACUGGAAC AACAAAGAGGCUCUGGUGGAAUUCAAGGAC GCCCACGCCAAGCGGCAGACCGUGGUGGUG CUGGGAUCUCAGGAAGGCGCCGUGCAUACA GCUCUGGCAGGCGCCCUGGAAGCCGAAAUG GAUGGCGCCAAAGGCAGACUGUCCAGCGGC CACCUGAAGUGCCGGCUGAAGAUGGACAAG CUGCGGCUGAAGGGCGUGUCCUACUCCCUG UGUACCGCCGCCUUCACCUUCACCAAGAUC CCCGCCGAGACACUGCACGGCACCGUGACU GUGGAAGUGCAGUACGCCGGCACCGACGGC CCUUGUAAAGUGCCUGCUCAGAUGGCCGUG GAUAUGCAGACCCUGACCCCUGUGGGCAGA CUGAUCACCGCCAACCCCGUGAUCACCGAG AGCACCGAGAACAGCAAGAUGAUGCUGGAA CUGGACCCCACCCUUCGGCGACAGCUACAUC GUGAUCGGCGUGGGAGAGAAGAAGAUCACC CACCACUGGCACAGAAGCGGCAGCACCAUC GGCAAGGCCUUUGAGGCUACAGUGCGGGGA | ZIKV prME Brazil Isolate (protein), with T76R, Q77E, W101R, L107R mutations <u>MWLVSLAIVTACAGAA</u>EVTRRGSAYYMYLDR NDAGEAISFPTTLGMNKCYIQIMDLGHMCDA TMSYECPMLDEGVEPDDVDCWCNTTSTWVVY GTCHHKKGEARRSRRAVTLPSHSTRKLQTRS QTWLESREYTKHLIRVENWIFRNPGFALAAA AIAWLLGSSTSQKVIYLVMILLIAPAYSIRC IGVSNRDFVEGMSGGTWVDVVLEHGGCVTVM AQDKPTVDIELVTTTVSNMAEVRSYCYEASI SDMASDSRCPREGEAYLDKQSDTQYVCKRTL VDRGRGNGCGRFGKGSLVTCAKFACSKKMTG KSIQPENLEYRIMLSVHGSQHSGMIVNDTGH ETDENRAKVEITPNSPRAEATLGGFGSLGLD CEPRTGLDFSDLYYLTMNNKHWLVHKEWFHD IPLPWHAGADTGTPHWNNKEALVEFKDAHAK RQTVVVLGSQEGAVHTALAGALEAEMDGAKG RLSSGHLKCRLKMDKLRLKGVSYSLCTAAFT FTKIPAETLHGTVTVEVQYAGTDGPCKVPAQ MAVDMQTLTPVGRLITANPVITESTENSKMM LELDPPFGDSYIVIGVGEKKITHHWHRSGST IGKAFEATVRGAKRMAVLGDTAWDFGSVGGA LNSLGKGIHQIFGAAFKSLFGGMSWFSQILI GTLLMWLGLNTKNGSISLMCLALGGVLIFLS TAVSA (SEQ ID NO: 8) |

TABLE 1-continued

ZIKV mRNA Vaccine Sequences

| ORF (with JEV signal sequence underlined) | Protein (with JEV signal sequence underlined) |
|---|---|
| GCCAAGAGAAUGGCCGUGCUGGGAGAUACC GCCUGGGACUUUGGCUCUGUGGGCGGAGCC CUGAACUCUCUGGGCAAGGGAAUCCACCAG AUCUUCGGAGCCGCCUUUAAGAGCCUGUUC GGCGGCAUGAGCUGGUUCAGCCAGAUCCUG AUCGGCACCCUGCUGAUGUGGCUGGGCCUG AACACCAAGAACGGCAGCAUCUCCCUGAUG UGCCUGGCUCUGGGAGGCGUGCUGAUCUUC CUGAGCACAGCCGUGUCUGCC (SEQ ID NO: 2) | |
| ZIKV prME Micronesia Isolate (mRNA) AUGUGGCUGGUGAGCCUGGCCAUCGUGACC GCCUGCGCCGGCGCCGUGGAGGUGACCAGA AGAGGCAGCGCCUACUACAUGUACCUGGAC AGAAGCGACGCCGGCGAGGCCAUCAGCUUC CCUACCACCCUGGGCAUGAACAAGUGCUAC AUCCAGAUCAUGGACCUGGGCCACAUGUGC GACGCCACCAUGAGCUACGAGUGCCCUAUG CUGGACGAGGGCGUGGAGCCUGACGACGUG GACUGCUGGUGCAACACCACCAGCACCUGG GUGGUGUACGGCACCUGCCACCACAAGAAG GGAGAGGCGAGAAGAAGCAGGAGAGCCGUG ACCCUGCCUAGCCACAGCACCAGAAAGCUG CAGACCCGGAGCCAGACCUGGCUGGAGAGC AGAGAGUACACCAAGCACCUGAUCAGAGUG GAGAACUGGAUCUUCAGAAACCCUGGCUUC GCCCUGGCCGCGGCUGCUAUCGCCUGGCUG CUGGGUAGUUCAACCAGCCAGAAGGUGAUC UACCUGGUGAUGAUCCUGCUGAUCGCCCCG GCAUACAGCAUCCGCUGCAUCGGCGUGAGC AACAGAGACUUCGUGGAGGGCAUGAGCGGA GGAACGUGGGUUGACGUGGUGCUGGAGCAC GGCGGCUGCGUGACCGUGAUGGCCCAGGAC AAGCCUGCCGUGGACAUCGAGCUGGUGACC ACCACCGUAUCCAACAUGGCCGAGGUGAGA AGCUACUGCUACGAGGCUAGCAUAAGCGAC AUGGCCAGCGACAGCCGAUGCCCCUACCCAG GGAGAAGCCUACCUGGACAAGCAGAGCGAC ACCCAGUACGUGUGCAAGAGAACCCUGGUG GACAGAGGCUGGGGCAACGGCUGCGGCCUG UUCGGCAAGGGCAGCCUGGUUACUUGCGCC AAGUUCGCCUGCAGCAAGAAGAUGACCGGC AAGAGCAUCCAGCCUGAGAACCUGGAGUAC AGAAUCAUGCUGAGCGUGCACGGCAGCCAG CACAGCGGCAUGAUCGUGAACGACACCGGC CACGAAACAGACGAGAACAGAGCCAAGGUG GAGAUCACCCCUAACAGCCCUAGAGCCGAG GCCACCCUUGGCGGCUUCGGCAGCCUCGGC CUGGACUGCGAGCCUAGAACGGGCCUGGAU UUCAGCGACCUGUACUACCUGACUAUGAAU AACAAGCACUGGCUUGUUCACAAGGAGUGG UUCCACGACAUCCCUCUGCCUUGGCACGCG GGAGCUGACACAGGAACCCCUCACUGGAAC AACAAGGAGGCCCUAGUUGAGUUCAAGGAC GCCCACGCCAAGAGACAGACCGUGGUCGUG CUGGGUUCCCAAGAGGGCGCUGUCCACACU GCACUCGCUGGCGCCCUGGAGGCCGAGAUG GACGGCGCCAAGGGAAGACUGAGCAGCGGC CACCUGAAGUGCAGGCUGAAGAUGGACAAG CUGCGGCUGAAAGGCGUGUCCUACAGCCUG UGCACCGCCGCCUUCACCUUCACCAAGAUC CCUGCCGAGACACUACACGGCACAGUGACC GUCGAGGUGCAGUACGCCGGCACCGACGGC CCUUGCAAGGUGCCUGCCCAGAUGGCCGUC GAUAUGCAAACUCUGACCCCUGUGGGACGG CUUAUCACCGCCAACCCUGUGAUUACUGAG AGCACCGAGAAUAGCAAGAUGAUGUUGGAA CUGGACCCUCCUUUCGGCGACAGCUACAUC GUGAUUGGAGUUGGAGAGAAGAAGAUCACA CACCACUGGCACAGAUCUGGAUCUACUAUU GGCAAGGCCUUCGAGGCAACAGUGAGAGGA GCAAAGAGAAUGGCAGUUCUGGGAGACACC GCCUGGGAUUUCGGAAGCGUAGGAGGUGCA | ZIKV prME Micronesia Isolate (protein) MWLVSLAIVTACAGAVEVTRRGSAYYMYLDR SDAGEAISFPTTLGMNKCYIQIMDLGHMCDA TMSYECPMLDEGVEPDDVDCWCNTTSTWVVY GTCHHKKGEARRSRRAVTLPSHSTRKLQTRS QTWLESREYTKHLIRVENWIFRNPGFALAAA AIAWLLGSSTSQKVIYLVMILLIAPAYSIRC IGVSNRDFVEGMSGGTWVDVVLEHGGCVTVM AQDKPAVDIELVTTTVSNMAEVRSYCYEASI SDMASDSRCPTQGEAYLDKQSDTQYVCKRTL VDRGWGNGCGLFGKGSLVTCAKFACSKKMTG KSIQPENLEYRIMLSVHGSQHSGMIVNDTGH ETDENRAKVEITPNSPRAEATLGGFGSLGLD CEPRTGLDFSDLYYLTMNNKHWLVHKEWFHD IPLPWHAGADTGTPHWNNKEALVEFKDAHAK RQTVVVLGSQEGAVHTALAGALEAEMDGAKG RLSSGHLKCRLKMDKLRLKGVSYSLCTAAFT FTKIPAETLHGTVTVEVQYAGTDGPCKVPAQ MAVDMQTLTPVGRLITANPVITESTENSKMM LELDPPFGDSYIVIGVGEKKITHHWHRSGST IGKAFEATVRGAKRMAVLGDTAWDFGSVGGA LNSLGKGIHQIFGAAFKSLFGGMSWFSQILI GTLLVWLGLNTKNGSISLTCLALGGVLIFLS TAVSA (SEQ ID NO: 9) |

TABLE 1-continued

ZIKV mRNA Vaccine Sequences

| ORF (with JEV signal sequence underlined) | Protein (with JEV signal sequence underlined) |
|---|---|
| UUGAACUCCCUAGGAAAGGGAAUCCACCAG AUCUUCGGAGCUGCAUUCAAGAGCCUAUUC GGCGGAAUGUCCUGGUUCAGCCAGAUCCUG AUCGGCACCCUGCUUGUGUGGCUUGGAUUG AACACCAAGAACGGUAGUAUUAGUCUGACC UGCCUGGCUCUCGGCGGUGUGCUGAUCUUC CUGAGUACUGCGGUGAGCGCC (SEQ ID NO: 3) | |
| ZIKV prME Micronesia Isolate (mRNA), with T76R, Q77E, W101R, L107R mutations AUGUGGCUGGUGAGCCUGGCCAUCGUGACC GCCUGCGCCGGCGCCGUGGAGGUGACCAGA AGAGGCAGCGCCUACUACAUGUACCUGGAC AGAAGCGACGCCGGCGAGGCCAUCAGCUUC CCUACCACCCUGGGCAUGAACAAGUGCUAC AUCCAGAUCAUGGACCUGGGCCACAUGUGC GACGCCACCAUGAGCUACGAGUGCCCUAUG CUGGACGAGGGCGUGGAGCCUGACGACGUG GACUGCUGGUGCAACACCACCAGCACCUGG GUGGUGUACGGCACCUGCCACCACAAGAAG GGCGAGGCCAGAAGAAGCAGAAGAGCCGUG ACCCUGCCUAGCCACAGCACCAGAAAGCUG CAGACCAGAAGCCAGACCUGGCUGGAGAGC AGAGAGUACACCAAGCACCUGAUCAGAGUG GAGAACUGGAUCUUCAGAAACCCUGGCUUC GCCCUGGCCGCCGCCGCCAUCGCCUGGCUG CUGGGCAGCAGCACCAGCCAGAAGGUGAUC UACCUGGUGAUGAUCCUGCUGAUCGCCCCU GCCUACAGCAUCAGAUGCAUCGGCGUGAGC AACAGAGACUUCGUGGAGGGCAUGAGCGGC GGCACCUGGGUGGACGUGGUGCUGGAGCAC GGCGGCUGCGUGACCGUGAUGGCCCAGGAC AAGCCUGCCGUGGACAUCGAGCUGGUGACC ACCACCGUGAGCAACAUGGCCGAGGUGAGA AGCUACUGCUACGAGGCCAGCAUCAGCGAC AUGGCCAGCGACAGCAGAUGCCCUAGAGAG GGCGAGGCCUACCUGGACAAGCAGAGCGAC ACCCAGUACGUGUGCAAGAGAACCCUGGUG GACAGAGGCAGAGGCAACGGCUGCGGCAGA UUCGGCAAGGGCAGCCUGGUGACCUGCGCC AAGUUCGCCUGCAGCAAGAAGAUGACCGGC AAGAGCAUCCAGCCUGAGAACCUGGAGUAC AGAAUCAUGCUGAGCGUGCACGGCAGCCAG CACAGCGGCAUGAUCGUGAACGACACCGGC CACGAGACCGACGAGAACAGAGCCAAGGUG GAGAUCACCCCUAACAGCCCUAGAGCCGAG GCCACCCUGGGCGGCUUCGGCAGCCUGGGC CUGGACUGCGAGCCUAGAACCGGCCUGGAC UUCAGCGACCUGUACUACCUGACCAUGAAC AACAAGCACUGGCUGGUGCACAAGGAGUGG UUCCACGACAUCCCUCUGCCUUGGCACGCC GGCGCCGACACCGGCACCCCUCACUGGAAC AACAAGGAGGCCCUGGUGGAGUUCAAGGAC GCCCACGCCAAGAGACAGACCGUGGUGGUG CUGGGCAGCCAGGAGGGCGCCGUGCACACC GCCCUGGCCGGCGCCCUGGAGGCCGAGAUG GACGGCGCCAAGGGCAGACUGAGCAGCGGC CACCUGAAGUGCAGACUGAAGAUGGACAAG CUGAGACUGAAGGGCGUGAGCUACAGCCUG UGCACCGCCGCCUUCACCUUCACCAAGAUC CCUGCCGAGACCCUGCACGGCACCGUGACC GUGGAGGUGCAGUACGCCGGCACCGACGGC CCUUGCAAGGUGCCUGCCCAGAUGGCCGUG GACAUGCAGACCCUGACCCCUGUGGGCAGA CUGAUCACCGCCAACCCUGUGAUCACCGAG AGCACCGAGAACAGCAAGAUGAUGCUGGAG CUGGACCCUCCUUUCGGCGACAGCUACAUC GUGAUCGGCGUGGGCGAGAAGAAGAUCACC CACCACUGGCACAGAAGCGGCAGCACCAUC GGCAAGGCCUUCGAGGCCACCGUGAGAGGC GCCAAGAGAAUGGCCGUGCUGGGCGACACC GCCUGGGACUUCGGCAGCGUGGGCGGCGCC CUGAACAGCCUGGGCAAGGGCAUCCACCAG | ZIKV prME Micronesia Isolate (protein), with T76R, Q77E, W101R, L107R mutations MWLVSLAIVTACAGAVEVTRRGSAYYMYLDR SDAGEAISFPTTLGMNKCYIQIMDLGHMCDA TMSYECPMLDEGVEPDDVDCWCNTTSTWVVY GTCHHKKGEARRSRRAVTLPSHSTRKLQTRS QTWLESREYTKHLIRVENWIFRNPGFALAAA AIAWLLGSSTSQKVIYLVMILLIAPAYSIRC IGVSNRDFVEGMSGGTWVDVVLEHGGCVTVM AQDKPAVDIELVTTTVSNMAEVRSYCYEASI SDMASDSRCPREGEAYLDKQSDTQYVCKRTL VDRRGNGCGRFGKGSLVTCAKFACSKKMTG KSIQPENLEYRIMLSVHGSQHSGMIVNDTGH ETDENRAKVEITPNSPRAEATLGGFGSLGLD CEPRTGLDFSDLYYLTMNNKHWLVHKEWFHD IPLPWHAGADTGTPHWNNKEALVEFKDAHAK RQTVVVLGSQEGAVHTALAGALEAEMDGAKG RLSSGHLKCRLKMDKLRLKGVSYSLCTAAFT FTKIPAETLHGTVTVEVQYAGTDGPCKVPAQ MAVDMQTLTPVGRLITANPVITESTENSKMM LELDPPFGDSYIVIGVGEKKITHHWHRSGST IGKAFEATVRGAKRMAVLGDTAWDFGSVGGA LNSLGKIHQIFGAAFKSLFGGMSWFSQILI GTLLVWLGLNTKNGSISLTCLALGGVLIFLS TAVSA (SEQ ID NO: 10) |

TABLE 1-continued

ZIKV mRNA Vaccine Sequences

| ORF (with JEV signal sequence underlined) | Protein (with JEV signal sequence underlined) |
|---|---|
| AUCUUCGGCGCCGCCUUCAAGAGCCUGUUC GGCGGCAUGAGCUGGUUCAGCCAGAUCCUG AUCGGCACCCUGCUGGUGUGGCUGGGCCUG AACACCAAGAACGGCAGCAUCAGCCUGACC UGCCUGGCCCUGGGCGGCGUGCUGAUCUUC CUGAGCACCGCCGUGAGCGCC (SEQ ID NO: 4) | |

| ZIKV prME Africa Isolate (mRNA) | ZIKV prME Africa Isolate (protein) |
|---|---|
| AUGUGGCUGGUGAGCCUGGCCAUCGUGACA GCGUGCGCUGGAGCCGCCGAGAUCACCAGA AGAGGCAGCGCCUACUACAUGUACCUGGAC AGAAGCGACGCCGGCAAGGCCAUCAGCUUC GCCACCACCCUGGGCGUGAACAAGUGCCAC GUGCAGAUCAUGGACCUGGGCCACAUGUGC GACGCCACCAUGAGCUACGAGUGCCCUAUG CUGGACGAGGGCGUGGAGCCUGACGACGUG GACUGCUGGUGCAACACCACCAGCACCUGG GUGGUGUACGGCACCUGCCACCACAAGAAG GGCGAGGCCAGAAGAAGCAGACGUGCCGUG ACCCUGCCUAGCCACAGCACCAGAAAGCUG CAGACCAGAAGCCAGACCUGGCUGGAGAGC AGAGAGUACACCAAGCACCUGAUCAAGGUG GAGAACUGGAUCUUCAGAAACCCUGGCUUC GCCCUGGUGGCCGUGGCAAUUGCCUGGCUG CUGGGCAGCUCCACAAGCCAGAAGGUGAUC UACCUGGUGAUGAUCCUGCUGAUCGCUCCA GCCUACAGCAUCCGAUGCAUCGGCGUGAGC AACAGAGACUUCGUGGAGGGCAUGAGCGGC GGAACCUGGGUUGACGUGGUGCUGGAGCAC GGCGGCUGCGUGACCGUGAUGGCCCAGGAC AAGCCUACCGUGGACAUCGAGCUGGUGACC ACCACCGUUAGCAACAUGGCCGAGGUGAGA AGCUACUGCUACGAGGCAUCCAUCAGCGAC AUGGCCAGCGACAGCCGCUGCCCUACCCAG GGCGAAGCAUACCUCGAUAAGCAGAGCGAC ACCCAGUACGUGUGCAAGAGAACUCUCGUG GACAGAGGCUGGGGCAACGGCUGCGGCCUG UUCGGCAAGGGCAGCCUGGUGACUUGCGCC AAGUUCACCUGCAGCAAGAAGAUGACCGGC AAGAGCAUCCAGCCUGAGAACCUGGAGUAC AGAAUCAUGCUGAGCGUGCACGGCAGCCAG CACAGCGGCAUGAUCGGCUACGAAACUGAC GAGGACAGAGCCAAGGUCGAAGUGACCCCU AACAGCCCUAGAGCCGAGGCCACCCUUGGA GGCUUCGGCUCCCUCGGCCUGGACUGCGAG CCUAGAACAGGACUCGACUUCAGCGACCUG UACUACCUGACCAUGAACAACAAGCACUGG CUGGUCCACAAGGAGUGGUUCCACGACAUC CCUCUGCCUUGGCACGCCGGAGCAGACACC GGCACCCCUCACUGGAAUAACAAGGAGGCG CUUGUGGAGUUCAAGGACGCCCACGCCAAG AGACAGACCGUGGUUGUGCUCGGAAGUCAG GAGGGCGCCGUGCACACCGCCCUGGCCGGA GCCCUGGAGGCCGAGAUGGACGGCGCAAAG GGCAGACUGUUCAGCGGCCACCUGAAGUGC AGACUGAAGAUGGACAAGCUGAGACUUAAG GGCGUCAGCUACAGCCUGUGCACCGCCGCC UUCACCUUCACCAAGGUGCCUGCCGAAACC CUGCACGGAACUGUAACCGUAGAGGUCCAG UACGCAGGAACCGACGGCCCUUGCAAGAUC CCUGUGCAGAUGGCGGUGGAUAUGCAGACC CUGACCCCUGUUGGCCGUUUGAUCACCGCC AACCCUGUGAUAACCGAGAGCACCGAGAAC AGCAAGAUGAUGCUGGAACUGGACCCUCCU UUCGGCGACAGCUACAUCGUGAUCGGAGUG GGCGAUAAGAAGAUCACCCACCACUGGCAU CGCAGCGGUUCUACCAUCGGAAAGGCCUUC GAAGCUACCGUUAGAGGUGCAAAGCGCAUG GCAGUCUUAGGUGACACCGCCUGGGACUUC GGUUCUGUCGGAGGCGUGUUCAACAGUCUG GGCAAGGGAAUCCACCAGAUCUUCGGCGCU GCCUUCAAGUCUUUGUUCGGAGGUAUGUCU UGGUUCAGCCAGAUCCUGAUCGGCACCCUU CUGGUUUGGCUGGGCCUCAACACCAAGAAC | MWLVSLAIVTACAGAAEITRRGSAYYMYLDR SDAGKAISFATTLGVNKCHVQIMDLGHMCDA TMSYECPMLDEGVEPDDVDCWCNTTSTWVVY GTCHHKKGEARRSRRAVTLPSHSTRKLQTRS QTWLESREYTKHLIKVENWIFRNPGFALVAV AIAWLLGSSTSQKVIYLVMILLIAPAYSIRC IGVSNRDFVEGMSGGTWVDVVLEHGGCVTVM AQDKPTVDIELVTTTVSNMAEVRSYCYEASI SDMASDSRCPTQGEAYLDKQSDTQYVCKRTL VDRGWGNGCGLFGKGSLVTCAKFTCSKKMTG KSIQPENLEYRIMLSVHGSQHSGMIGYETDE DRAKVEVTPNSPRAEATLGGFGSLGLDCEPR TGLDFSDLYYLTMNNKHWLVHKEWFHDIPLP WHAGADTGTPHWNNKEALVEFKDAHAKRQTV VVLGSQEGAVHTALAGALEAEMDGAKGRLFS GHLKCRLKMDKLRLKGVSYSLCTAAFTFTKV PAETLHGTVTVEVQYAGTDGPCKIPVQMAVD MQTLTPVGRLITANPVITESTENSKMMLELD PPFGDSYIVIGVGDKKITHHWHRSGSTIGKA FEATVRGAKRMAVLGDTAWDFGSVGGVFNSL GKGIHQIFGAAFKSLFGGMSWFSQILIGTLL VWLGLNTKNGSISLTCLALGGVMIFLSTAVS A (SEQ ID NO: 11) |

TABLE 1-continued

ZIKV mRNA Vaccine Sequences

| ORF (with JEV signal sequence underlined) | Protein (with JEV signal sequence underlined) |
|---|---|
| GGAUCCAUAUCCCUGACCUGCCUGGCCUUG GGCGGUGUCAUGAUCUUCCUGUCGACUGCC GUGAGCGCC (SEQ ID NO: 5) | |
| ZIKV prME Africa Isolate (mRNA), with T76R, Q77E, W101R, L107R mutations AUGUGGCUGGUGAGCCUGGCCAUCGUGACU GCUUGCGCGGGUGCCGCCGAGAUCACCAGA AGAGGCAGCGCCUACUACAUGUACCUGGAC AGAAGCGACGCCGGCAAGGCCAUCAGCUUC GCCACCACCCUGGGCGUGAACAAGUGCCAC GUGCAGAUCAUGGACCUGGGCCACAUGUGC GACGCCACCAUGAGCUACGAGUGCCCUAUG CUGGACGAGGGCGUGGAGCCUGACGACGUG GACUGCUGGUGCAACACCACCAGCACCUGG GUGGUGUACGGCACCUGCCACCACAAGAAG GGCGAGGCCAGAAGAAGCAGGAGGGCCGUG ACCCUGCCUAGCCACAGCACCAGAAAGCUG CAGACCAGAAGCCAGAACCUGGCUGGAGAGC AGAGAGUACACCAAGCACCUGAUCAAGGUG GAGAACUGGAUCUUCAGAAACCCUGGCUUC GCCCUGGUGGCCGUGGCUAUAGCCUGGCUG CUGGGAUCUUCAACAAGCCAGAAGGUGAUC UACUUGGUGAUGAUCCUGCUGAUCGCGCCA GCCUACAGCAUCCGCUGCAUCGGCGUGAGC AACAGAGACUUCGUGGAGGGCAUGAGCGGC GGAACUUGGGUGGACGUGGUGCUGGAGCAC GGCGGCUGCGUGACCGUGAUGGCCCAGGAC AAGCCUACCGUGGACAUCGAGCUGGUGACC ACCACGGUUUCUAAUAUGGCCGAGGUGAGA AGCUACUGCUACGAGGCAUCCAUCAGCGAC AUGGCCAGCGACAGCAGGUGCCCUAGAGAA GGAGAAGCCUAUCUCGACAAGCAGAGCGAC ACCCAGUACGUGUGCAAGAGAACCCUCGUG GACAGAGGCAGAGGCAACGGCUGCGGCAGA UUCGGCAAGGGCAGCCUGGUUACGUGCGCC AAGUUCACCUGCAGCAAGAAGAUGACCGGC AAGAGCAUCCAGCCUGAGAACCUGGAGUAC AGAAUCAUGCUGAGCGUGCACGGCAGCCAG CACAGCGGCAUGAUCGGCUACGAGACAGAC GAGGACAGAGCUAAGGUCGAGGUGACCCCU AACUCCCCACGCGCCGAGGCUACGCUGGGA GGCUUCGGAUCUCUGGGCCUGGACUGCGAG CCUAGAACCGGCUUGGAUUUCAGCGACCUG UACUACCUGACCAUGAACAACAAGCACUGG UUGGUCCACAAGGAGUGGUUCCACGACAUC CCUCUGCCUUGGCACGCGGGCGCUGACACC GGCACCCCUCACUGGAAUAACAAGGAGGCC UUGGUGGAGUUCAAGGACGCCCACGCCAAG AGACAGACCGUGGUGGUCUUGGGUUCCCAG GAGGGCGCCGUGCACACCGCCCUGGCAGGA GCUCUGGAGGCCGAGAUGGACGGCGCCAAG GGUAGACUGUUCAGCGGCCACCUGAAGUGC AGACUGAAGAUGGAUAAGCUGAGACUCAAG GGUGUGUCAUACAGCCUGUGCACCGCCGCC UUCACCUUCACCAAGGUGCCUGCCGAAACC CUGCACGGAACCGUGACUGUAGAGGUACAG UACGCUGGCACCGACGGCCCUUGCAAGAUC CCUGUGCAGAUGGCCGUUGACAUGCAGACC CUGACCCCUGUGGGCAGGCUGAUCACCGCC AACCCUGUGAUCACUGAGAGCACCGAGAAC AGCAAGAUGAUGCUGGAACUGGACCCUCCU UUCGGCGACAGCUACAUCGUGAUAGGCGUG GGCGAUAAGAAGAUCACCCACCAUUGGCAC AGAAGUGGUUCGACUAUCGGUAAGGCAUUC GAAGCUACAGUGAGAGGAGCCAAGAGGAUG GCAGUGCUGGGUGACACCGCCUGGGAUUUC GGUUCAGUGGGCGGCGUGUUCAAUUCCCUG GGCAAGGGUAUCCACCAGAUCUUCGGCGCU GCCUUCAAGAGCCUGUUCGGUGGAAUGAGC UGGUUCAGCCAGAUCCUGAUCGGCACCCUC | ZIKV prME Africa Isolate (protein), with T76R, Q77E, W101R, L107R mutations MWLVSLAIVTACAGAAEITRRGSAYYMYLDR SDAGKAISFATTLGVNKCHVQIMDLGHMCDA TMSYECPMLDEGVEPDDVDCWCNTTSTWVVY GTCHHKKGEARRSRRAVTLPSHSTRKLQTRS QTWLESREYTKHLIKVENWIFRNPGFALVAV AIAWLLGSSTSQKVIYLVMILLIAPAYSIRC IGVSNRDFVEGMSGGTWVDVVLEHGGCVTVM AQDKPTVDIELVTTTVSNMAEVRSYCYEASI SDMASDSRCPREGEAYLDKQSDTQYVCKRTL VDRGRGNGCGRFGKGSLVTCAKFTCSKKMTG KSIQPENLEYRIMLSVHGSQHSGMIGYETDE DRAKVEVTPNSPRAEATLGGFGSLGLDCEPR TGLDFSDLYYLTMNNKHWLVHKEWFHDIPLP WHAGADTGTPHWNNKEALVEFKDAHAKRQTV VVLGSQEGAVHTALAGALEAEMDGAKGRLFS GHLKCRLKMDKLRLKGVSYSLCTAAFTFTKV PAETLHGTVTVEVQYAGTDGPCKIPVQMAVD MQTLTPVGRLITANPVITESTENSKMMLELD PPFGDSYIVIGVGDKKITHHWHRSGSTIGKA FEATVRGAKRMAVLGDTAWDFGSVGGVFNSL GKGIHQIFGAAFKSLFGGMSWFSQILIGTLL VWLGLNTKNGSISLTCLALGGVMIFLSTAVS A (SEQ ID NO: 12) |

TABLE 1-continued

| ZIKV mRNA Vaccine Sequences | |
|---|---|
| ORF (with JEV signal sequence underlined) | Protein (with JEV signal sequence underlined) |
| CUGGUUUGGCUUGGUUUGAACACCAAGAAC GGCUCUAUUUCCCUGACCUGCCUGGCACUA GGAGGCGUCAUGAUAUUCCUGAGUACCGCC GUGAGCGCC (SEQ ID NO: 6) | |

Any of the open reading frames (ORFs) provided in Table 1 may include any of the following 5' UTR sequences or other 5' UTR sequence (e.g., wild-type 5' UTR sequence):

(SEQ ID NO: 13)
GGGAAAUAAGAGAGAAAAGAAGAGUAAGAAGAAAUAUAAGACCCCGGCGC
CGCCACC (SEQ ID NO: 14)
GGGAAAUAAGAGAGAAAAGAAGAGUAAGAAGAAAUAUAAGAGCCACC.

Likewise, any of the ORFs provided in Table 1 may include any of the following 3' UTR sequences or other 3' UTR sequence (e.g., wild-type 3' UTR sequence):

(SEQ ID NO: 15)
UGAUAAUAGGCUGGAGCCUCGGUGGCCUAGCUUCUUGCCCCUUGGGCCUC
CCCCCAGCCCCUCCUCCCCUUCCUGCACCCGUACCCCCGUGGUCUUUGAA
UAAAGUCUGAGUGGGCGGC (SEQ ID NO: 16)
UGAUAAUAGGCUGGAGCCUCGGUGGCCAUGCUUCUUGCCCCUUGGGCCUC
CCCCCAGCCCCUCCUCCCCUUCCUGCACCCGUACCCCCGUGGUCUUUGAA
UAAAGUCUGAGUGGGCGGC

Further, any of the ORFs provided in Table 1 may include a polyA tail (e.g., 100 nucleotides).

In some embodiments, a ZIKV mRNA vaccine (mRNA-1893) comprises the following sequence, including a 5' UTR, 3' UTR and polyA tail:

(SEQ ID NO: 20)
GGGAAAUAAGAGAGAAAAGAAGAGUAAGAAGAAAUAUAAGACCCCGGCGC
CGCCACCAUGUGGCUGGUGUCCCUGGCCAUCGUGACAGCCUGUGCUGGCG
CCGCUGAAGUGACCAGAAGAGGCAGCGCCUACUACAUGUACCUGGACCGG
AACGAUGCCGGCGAGGCCAUCAGCUUUCCAACCACCCUGGGCAUGAACAA
GUGCUACAUCCAGAUCAUGGACCUGGGCCACAUGUGCGACGCCACCAUGA
GCUACGAGUGCCCCAUGCUGGACGAGGGCGUGGAACCCGACGAUGUGGAC
UGCUGGUGCAACACCACCAGCACCUGGGUGGUGUACGGCACCUGUCACCA
CAAGAAGGGCGAAGCCAGACGGUCCAGACGGGCCGUGACACUGCCUAGCC
ACAGCACCAGAAAGCUGCAGACCCGGUCCCAGACCUGGCUGGAAAGCAGA
GAGUACACCAAGCACCUGAUCCGGGUGGAAAACUGGAUCUUCCGGAACCC
CGGCUUUGCCCUGGCCGCUGCUGCUAUUGCUUGGCUGCUGGGCAGCAGCA
CCUCCCAGAAAGUGAUCUACCUCGUGAUGAUCCUGCUGAUCGCCCCUGCC

-continued
UACAGCAUCCGGUGUAUCGGCGUGUCCAACCGGGACUUCGUGGAAGGCAU
GAGCGGCGGCACAUGGGUGGACGUGGUGCUGGAACAUGGCGGCUGCGUGA
CAGUGAUGGCCCAGGACAAGCCCACCGUGGACAUCGAGCUCGUGACCACC
ACCGUGUCCAAUAUGGCCGAAGUGCGGAGCUACUGCUACGAGGCCAGCAU
CAGCGACAUGGCCAGCGACAGCAGAUGCCCUACACAGGGCGAGGCCUACC
UGGACAAGCAGUCCGACACCCAGUACGUGUGCAAGCGGACCCUGGUGGAU
AGAGGCUGGGGCAAUGGCUGCGGCCUGUUUGGCAAGGGCAGCCUCGUGAC
CUGCGCCAAGUUCGCCUGCAGCAAGAAGAUGACCGGCAAGAGCAUCCAGC
CCGAGAACCUGGAAUACCGGAUCAUGCUGAGCGUGCACGGCAGCCAGCAC
UCCGGCAUGAUCGUGAACGACACCGGCCACGAGACAGACGAGAACCGGGC
CAAGGUGGAAAUCACCCCUAACAGCCCUAGAGCCGAGGCCACACUGGGCG
GCUUUGGAUCUCUGGGCCUGGACUGCGAGCCUAGAACCGGCCUGGAUUUC
AGCGACCUGUACUACCUGACCAUGAACAACAAGCACUGGCUGGUGCACAA
AGAGUGGUUCCACGACAUCCCUCUGCCCUGGCAUGCCGGCGCUGAUACAG
GCACACCCCACUGGAACAACAAAGAGGCUCUGGUGGAAUUCAAGGACGCC
CACGCCAAGCGGCAGACCGUGGUGGUGCUGGGAUCUCAGGAAGGCGCCGU
GCAUACAGCUCUGGCAGGCGCCCUGGAAGCCGAAAUGGAUGGCGCCAAAG
GCAGACUGUCCAGCGGCCACCUGAAGUGCCGGCUGAAGAUGGACAAGCUG
CGGCUGAAGGGCGUGUCCUACUCCCUGUGUACCGCCGCCUUCACCUUCAC
CAAGAUCCCCGCCGAGACACUGCACGGCACCGUGACUGUGGAAGUGCAGU
ACGCCGGCACCGACGGCCCUUGUAAAGUGCCUGCUCAGAUGGCCGUGGAU
AUGCAGACCCUGACCCCUGUGGGCAGACUGAUCACCGCCAACCCCGUGAU
CACCGAGAGCACCGAGAACAGCAAGAUGAUGCUGGAACUGGACCCACCCU
UCGGCGACAGCUACAUCGUGAUCGGCGUGGGAGAGAAGAAGAUCACCCAC
CACUGGCACAGAAGCGGCAGCACCAUCGGCAAGGCCUUUGAGGCUACAGU
GCGGGGAGCCAAGAGAAUGGCCGUGCUGGGAGAUACCGCCUGGGACUUUG
GCUCUGUGGGCGGAGCCCUGAACUCUCUGGGCAAGGGAAUCCACCAGAUC
UUCGGAGCCGCCUUUAAGAGCCUGUUCGGCGGCAUGAGCUGGUUCAGCCA
GAUCCUGAUCGGCACCCUGCUGAUGUGGCUGGGCCUGAACACCAAGAACG
GCAGCAUCUCCCUGAUGUGCCUGGCUCUGGGAGGCGUGCUGAUCUUCCUG
AGCACAGCCGUGUCUGCCUGAUAAUAGGCUGGAGCCUCGGUGGCCUAGCU
UCUUGCCCCUUGGGCCUCCCCCCAGCCCCUCCUCCCCUUCCUGCACCCGU
ACCCCCGUGGUCUUUGAAUAAAGUCUGAGUGGGCGGCAAAAAAAAAAAAA

EXAMPLES

Figure 2:
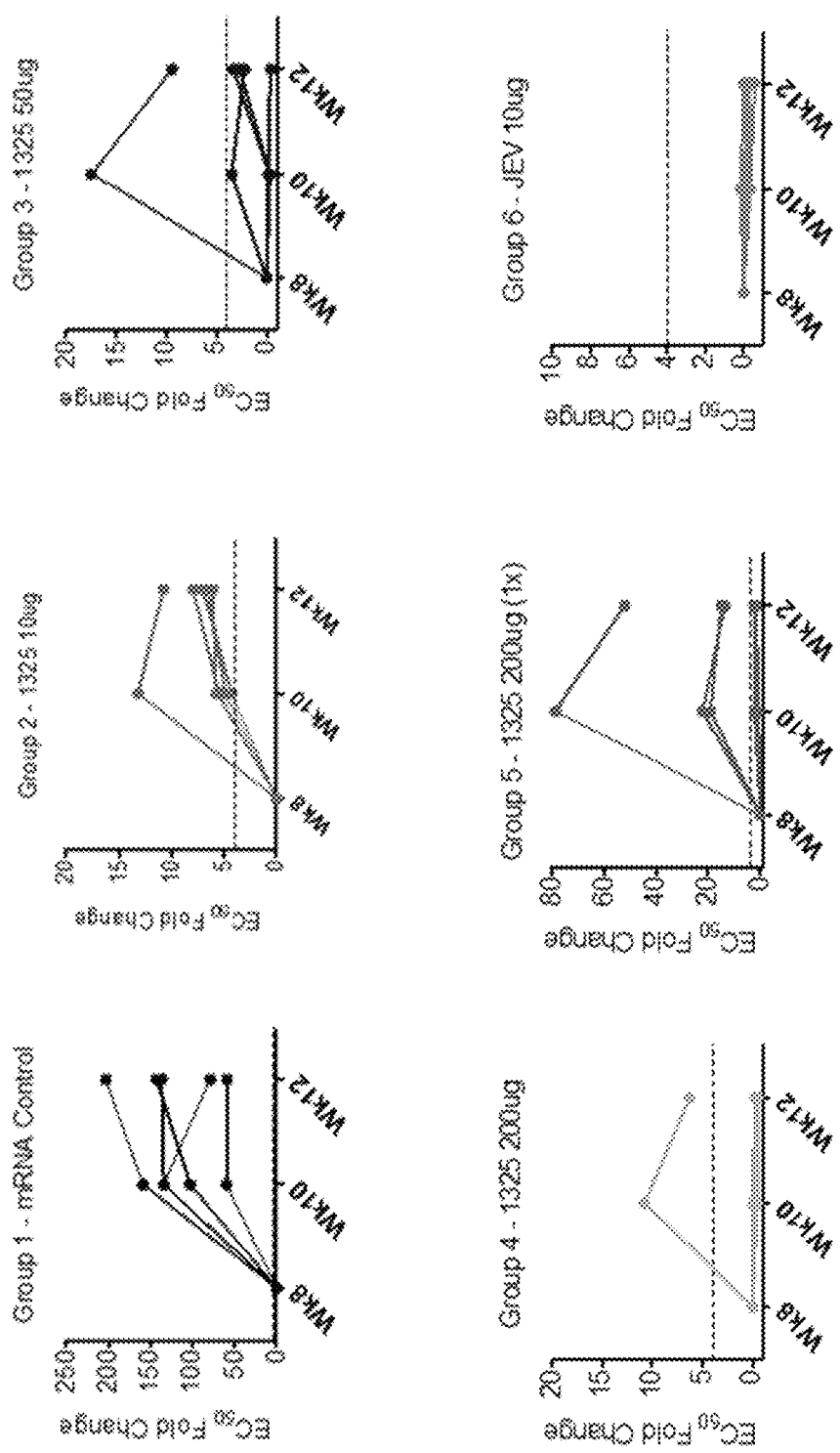
FIG. 2 includes graphs showing neutralizing antibody titers ($EC_{50}$ fold change relative to week 8) obtained from the same NHP experiments described in FIG. 1.

Non-human primates (n=5) were immunized intramuscularly (IM) with a vaccine composition comprising mRNA encoding either an IgE signal peptide fused to a ZIKV prME antigen (mRNA-1325, SEQ ID NO:17) (a single 200 µg dose, or a 10 µg, 50 µg or 200 µg dose followed by an equivalent boost at week 4, or a JEV signal peptide fused to a ZIKV prME antigen (mRNA-1893, SEQ ID NO:7) (a 10 µg followed by an equivalent boost at week 4). Animals were challenged at week 8 with 1000 focus-forming units (FFU) of Zika virus. Serum was collected 3, 4, 5, 6 and 7 days post challenge. The data in FIG. 1 shows that while a single 200 µg dose of the mRNA-1325 vaccine conferred nearly complete protection, the mRNA-1893 vaccine unexpectedly provided sterilizing immunity at a 20 fold lower dose. Neutralizing antibody titers ($EC_{50}$ fold change relative to week 8) are shown in FIG. 2.

mRNA-1325
(SEQ ID NO: 17)
MDWTWILFLVAAATRVHSVEVTRRGSAYYMYLDRSDAGEAISFPTTLGMN

KCYIQIMDLGHMCDATMSYECPMLDEGVEPDDVDCWCNTTSTWVVYGTCH

HKKGEARRSRRAVTLPSHSTRKLQTRSQTWLESREYTKHLIRVENWIFRN

PGFALAAAAIAWLLGSSTSQKVIYLVMILLIAPAYSIRCIGVSNRDFVEG

MSGGTWVDVVLEHGGCVTVMAQDKPAVDIELVTTTVSNMAEVRSYCYEAS

ISDMASDSRCPTQGEAYLDKQSDTQYVCKRTLVDRGWGNGCGLFGKGSLV

TCAKFACSKKMTGKSIQPENLEYRIMLSVHGSQHSGMIVNDTGHETDENR

AKVEITPNSPRAEATLGGFGSLGLDCEPRTGLDFSDLYYLTMNNKHWLVH

KEWFHDIPLPWHAGADTGTPHWNNKEALVEFKDAHAKRQTVVVLGSQEGA

VHTALAGALEAEMDGAKGRLSSGHLKCRLKMDKLRLKGVSYSLCTAAFTF

TKIPAETLHGTVTVEVQYAGTDGPCKVPAQMAVDMQTLTPVGRLITANPV

ITESTENSKMMLELDPPFGDSYIVIGVGEKKITHHWHRSGSTIGKAFEAT

VRGAKRMAVLGDTAWDFGSVGGALNSLGKGIHQIFGAAFKSLFGGMSWFS

QILIGTLLVWLGLNTKNGSISLTCLALGGVLIFLSTAVSA mRNA-1893
(SEQ ID NO: 7)
MWLVSLAIVTACAGAAEVTRRGSAYYMYLDRNDAGEAISFPTTLGMNKCY

IQIMDLGHMCDATMSYECPMLDEGVEPDDVDCWCNTTSTWVVYGTCHHKK

GEARRSRRAVTLPSHSTRKLQTRSQTWLESREYTKHLIRVENWIFRNPGF

ALAAAAIAWLLGSSTSQKVIYLVMILLIAPAYSIRCIGVSNRDFVEGMSG

GTWVDVVLEHGGCVTVMAQDKPTVDIELVTTTVSNMAEVRSYCYEASISD

MASDSRCPTQGEAYLDKQSDTQYVCKRTLVDRGWGNGCGLFGKGSLVTCA

KFACSKKMTGKSIQPENLEYRIMLSVHGSQHSGMIVNDTGHETDENRAKV

EITPNSPRAEATLGGFGSLGLDCEPRTGLDFSDLYYLTMNNKHWLVHKEW

FHDIPLPWHAGADTGTPHWNNKEALVEFKDAHAKRQTVVVLGSQEGAVHT

ALAGALEAEMDGAKGRLSSGHLKCRLKMDKLRLKGVSYSLCTAAFTFTKI

PAETLHGTVTVEVQYAGTDGPCKVPAQMAVDMQTLTPVGRLITANPVITE

STENSKMMLELDPPFGDSYIVIGVGEKKITHHWHRSGSTIGKAFEATVRG

AKRMAVLGDTAWDFGSVGGALNSLGKGIHQIFGAAFKSLFGGMSWFSQIL

IGTLLMWLGLNTKNGSISLMCLALGGVLIFLSTAVSA

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition comprising a messenger ribonucleic acid (mRNA) comprising a 5' untranslated region (UTR), an open reading frame (ORF) encoding a JEV signal peptide fused to a Zika virus (ZIKV) prME protein, and a 3' UTR, wherein the mRNA is formulated in a lipid nanoparticle, and the ORF comprises a nucleotide sequence having at least 98% identity to the nucleotide sequence of SEQ ID NO: 1.

2. The composition of claim 1, wherein the ORF comprises the nucleotide sequence of SEQ ID NO: 1.

3. The composition of claim 1, wherein the ZIKV prME protein comprises the amino acid sequence of SEQ ID NO: 7.

4. The composition of claim 1, wherein the mRNA comprises a chemical modification.

5. The composition of claim 4, wherein the chemical modification is 1-methyl-pseudouridine.

6. The composition of claim 1, wherein the lipid nanoparticle comprises an ionizable cationic lipid, a non-cationic lipid, a sterol, and a PEG-modified lipid.

7. The composition of claim 6, wherein the lipid nanoparticle comprises 20-60 mol % ionizable cationic lipid, 5-25 mol % non-cationic lipid, 25-55 mol % sterol, and 0.5-15 mol % PEG-modified lipid.

8. The composition of claim 6, wherein the ionizable cationic lipid comprises the following compound:

9. A method comprising administering to a subject the composition of claim 1 in an effective amount to induce in the subject a ZIKV-specific immune response.

10. A composition comprising a messenger ribonucleic acid (mRNA) comprising an open reading frame (ORF) encoding a Zika virus (ZIKV) prME protein, wherein the mRNA is formulated in a lipid nanoparticle, and the ORF comprises the nucleotide sequence of SEQ ID NO: 1.

11. The composition of claim 10, wherein the ZIKV prME protein comprises the amino acid sequence of SEQ ID NO: 7.

12. The composition of claim 10, wherein the mRNA further comprises a 5' UTR that comprises a sequence selected from SEQ ID NO: 13 and SEQ ID NO: 14.

13. The composition of claim 10, wherein the mRNA further comprises a 3' UTR that comprises a sequence selected from SEQ ID NO: 15 and SEQ ID NO: 16.

14. The composition of claim 10, wherein the mRNA comprises a chemical modification.

15. The composition of claim 14, wherein the chemical modification is 1-methyl-pseudouridine.

16. The composition of claim 10, wherein the lipid nanoparticle comprises an ionizable cationic lipid, a non-cationic lipid, a sterol, and a PEG-modified lipid.

17. The composition of claim 16, wherein the lipid nanoparticle comprises 20-60 mol % ionizable cationic lipid, 5-25 mol % non-cationic lipid, 25-55 mol % sterol, and 0.5-15 mol % PEG-modified lipid.

18. The composition of claim 17, wherein the ionizable cationic lipid comprises the following compound:

19. A method comprising administering to a subject the composition of claim 10 in an effective amount to induce in the subject a ZIKV prME-specific immune response.

20. The composition of claim 10, wherein the mRNA further comprises a 5' UTR that comprises the sequence of SEQ ID NO: 13 and a 3' UTR that comprises the sequence of SEQ ID NO: 15.

21. The composition of claim 10, wherein the mRNA further comprises a 5' UTR that comprises the sequence of SEQ ID NO: 14 and a 3' UTR that comprises the sequence of SEQ ID NO: 16.

22. The composition of claim 1, wherein the 5' UTR comprises a sequence selected from SEQ ID NO: 13 and SEQ ID NO: 14.

23. The composition of claim 1, wherein the 3' UTR comprises a sequence selected from SEQ ID NO: 15 and SEQ ID NO: 16.

24. The composition of claim 1, wherein the 5' UTR comprises the sequence of SEQ ID NO: 13 and the 3' UTR comprises the sequence of SEQ ID NO: 15.

25. The composition of claim 1, wherein the 5' UTR comprises the sequence of SEQ ID NO: 14 and the 3' UTR comprises the sequence of SEQ ID NO: 16.

* * * * *

UNITED STATES PATENT AND TRADEMARK OFFICE
CERTIFICATE OF CORRECTION

PATENT NO. : 11,207,398 B2
APPLICATION NO. : 16/848318
DATED : December 28, 2021
INVENTOR(S) : Giuseppe Ciaramella et al.

It is certified that error appears in the above-identified patent and that said Letters Patent is hereby corrected as shown below:

In the Claims

Column 64, Line 28-67 please replace claims with the following:

--11. The composition of claim 10, wherein the mRNA further comprises a 5' UTR that comprises a sequence selected from SEQ ID NO: 13 and SEQ ID NO: 14.

12. The composition of claim 10, wherein the mRNA further comprises a 3' UTR that comprises a sequence selected from SEQ ID NO: 15 and SEQ ID NO: 16.

13. The composition of claim 10, wherein the mRNA comprises a chemical modification.

14. The composition of claim 13, wherein the chemical modification is 1-methyl-pseudouridine.

15. The composition of claim 10, wherein the lipid nanoparticle comprises an ionizable cationic lipid, a non-cationic lipid, a sterol, and a PEG-modified lipid.

16. The composition of claim 15, wherein the lipid nanoparticle comprises 20-60 mol% ionizable cationic lipid, 5-25 mol% non-cationic lipid, 25-55 mol% sterol, and 0.5-15 mol% PEG-modified lipid.

17. The composition of claim 16, wherein the ionizable cationic lipid comprises the following compound:

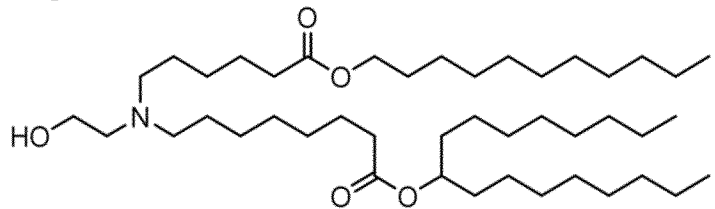

.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

18. A method comprising administering to a subject the composition of claim 10 in an effective amount to induce in the subject a ZIKV prME-specific immune response.

19. The composition of claim 10, wherein the mRNA further comprises a 5' UTR that comprises the sequence of SEQ ID NO: 13 and a 3' UTR that comprises the sequence of SEQ ID NO: 15.

20. The composition of claim 10, wherein the mRNA further comprises a 5' UTR that comprises the sequence of SEQ ID NO: 14 and a 3' UTR that comprises the sequence of SEQ ID NO: 16.

21. The composition of claim 1, wherein the 5' UTR comprises a sequence selected from SEQ ID NO: 13 and SEQ ID NO: 14.

22. The composition of claim 1, wherein the 3' UTR comprises a sequence selected from SEQ ID NO: 15 and SEQ ID NO: 16.

23. The composition of claim 1, wherein the 5' UTR comprises the sequence of SEQ ID NO: 13 and the 3' UTR comprises the sequence of SEQ ID NO: 15.

24. The composition of claim 1, wherein the 5' UTR comprises the sequence of SEQ ID NO: 14 and the 3' UTR comprises the sequence of SEQ ID NO: 16.--